US007799741B2

(12) United States Patent
Guzmann et al.

(10) Patent No.: US 7,799,741 B2
(45) Date of Patent: Sep. 21, 2010

(54) DRILLING MUD CONTAINING HYDROPHOBIN

(75) Inventors: Marcus Guzmann, Mühlhausen (DE); Yaqian Liu, Ludwigshafen (DE); Ulf Baus, Dossenheim (DE)

(73) Assignee: BASF SE (DE)

( * ) Notice: Subject to any disclaimer, the term of this patent is extended or adjusted under 35 U.S.C. 154(b) by 171 days.

(21) Appl. No.: 11/886,991

(22) PCT Filed: Mar. 29, 2006

(86) PCT No.: PCT/EP2006/061134

§ 371 (c)(1),
(2), (4) Date: Sep. 24, 2007

(87) PCT Pub. No.: WO2006/103253

PCT Pub. Date: Oct. 5, 2006

(65) Prior Publication Data

US 2009/0131281 A1    May 21, 2009

(30) Foreign Application Priority Data

Apr. 1, 2005  (EP) .................................. 05007208
Aug. 4, 2005  (EP) .................................. 05016962

(51) Int. Cl.
 C09K 8/36    (2006.01)
 C09K 8/22    (2006.01)
 C09K 8/54    (2006.01)
(52) U.S. Cl. .................. 507/129; 507/239; 507/268
(58) Field of Classification Search ................ 507/129, 507/239, 268
 See application file for complete search history.

(56) References Cited

U.S. PATENT DOCUMENTS

| 2,399,161 | A | 4/1946 | Brother et al. |
| 3,751,280 | A | 8/1973 | Nerurkar et al. |
| 4,129,706 | A | 12/1978 | Keppler et al. |
| 4,241,191 | A | 12/1980 | Keppler et al. |
| 5,015,677 | A | 5/1991 | Benedict et al. |
| 5,049,504 | A | 9/1991 | Maugh et al. |
| 5,110,835 | A | 5/1992 | Walter et al. |
| 5,290,819 | A | 3/1994 | Witt et al. |
| 5,859,198 | A | 1/1999 | Haber et al. |
| 6,977,239 | B1 | 12/2005 | Weuthen et al. |
| 2003/0049726 | A1 | 3/2003 | Holloway et al. |
| 2003/0113454 | A1 | 6/2003 | de Vocht et al. |
| 2003/0134042 | A1 | 7/2003 | de Vocht et al. |
| 2003/0217419 | A1 | 11/2003 | Vic |
| 2004/0238170 | A1* | 12/2004 | Fanguy et al. ............... 166/291 |
| 2006/0040349 | A1 | 2/2006 | Sweigard et al. |
| 2007/0077619 | A1 | 4/2007 | Ostermann et al. |

FOREIGN PATENT DOCUMENTS

| DE | 2609104 | A1 | 9/1977 |
| DE | 2638839 | A1 | 3/1978 |
| DE | 4220225 | A1 | 12/1993 |
| DE | 19942539 | A1 | 3/2001 |
| DE | 102004025805 | A1 | 12/2005 |
| DE | 102005007480 | A1 | 9/2006 |
| EP | 0252561 | A2 | 1/1988 |
| EP | 0470455 | A2 | 2/1992 |
| EP | 0611824 | A1 | 8/1994 |
| EP | 0662515 | A1 | 7/1995 |
| EP | 0773296 | A1 | 5/1997 |
| EP | 1010748 | A1 | 6/2000 |
| EP | 1223219 | A2 | 7/2002 |
| EP | 1252516 | B1 | 10/2002 |
| FR | 2833490 | A1 | 6/2003 |
| GB | 195876 | | 4/1923 |
| GB | 2235457 | | 3/1991 |
| JP | 60206893 | | 10/1985 |
| JP | 06327481 | | 11/1994 |
| JP | 07289261 | | 11/1995 |
| JP | 08266281 | | 10/1996 |
| JP | 11169177 | | 6/1999 |
| WO | WO-9409094 | A1 | 4/1994 |
| WO | WO-96/41882 | A1 | 12/1996 |
| WO | WO-0023039 | A2 | 4/2000 |
| WO | WO-00/58342 | A1 | 10/2000 |
| WO | WO-0138476 | A1 | 5/2001 |
| WO | WO-01/57528 | A1 | 8/2001 |
| WO | WO-01/60916 | A1 | 8/2001 |
| WO | WO-0157066 | A2 | 8/2001 |
| WO | WO-01/74864 | A1 | 10/2001 |
| WO | WO-0220651 | A2 | 3/2002 |
| WO | WO-0246342 | A2 | 6/2002 |
| WO | WO-0246369 | A2 | 6/2002 |

(Continued)

OTHER PUBLICATIONS

Stringer, M. A., et al., "dewA Encodes a Fungal Hydrophobin Component of the *Aspergillus* Spore Wall", Molecular Microbiology, 1995, vol. 16, No. 1, pp. 33-44.

(Continued)

*Primary Examiner*—Timothy J. Kugel
*Assistant Examiner*—Atnaf Admasu
(74) *Attorney, Agent, or Firm*—Connolly Bove Lodge & Hutz LLP

(57) ABSTRACT

The present invention relates to the use of at least one hydrophobin or at least one hydrophobin derivative in a drilling mud.

24 Claims, 1 Drawing Sheet

FOREIGN PATENT DOCUMENTS

Figure 1:
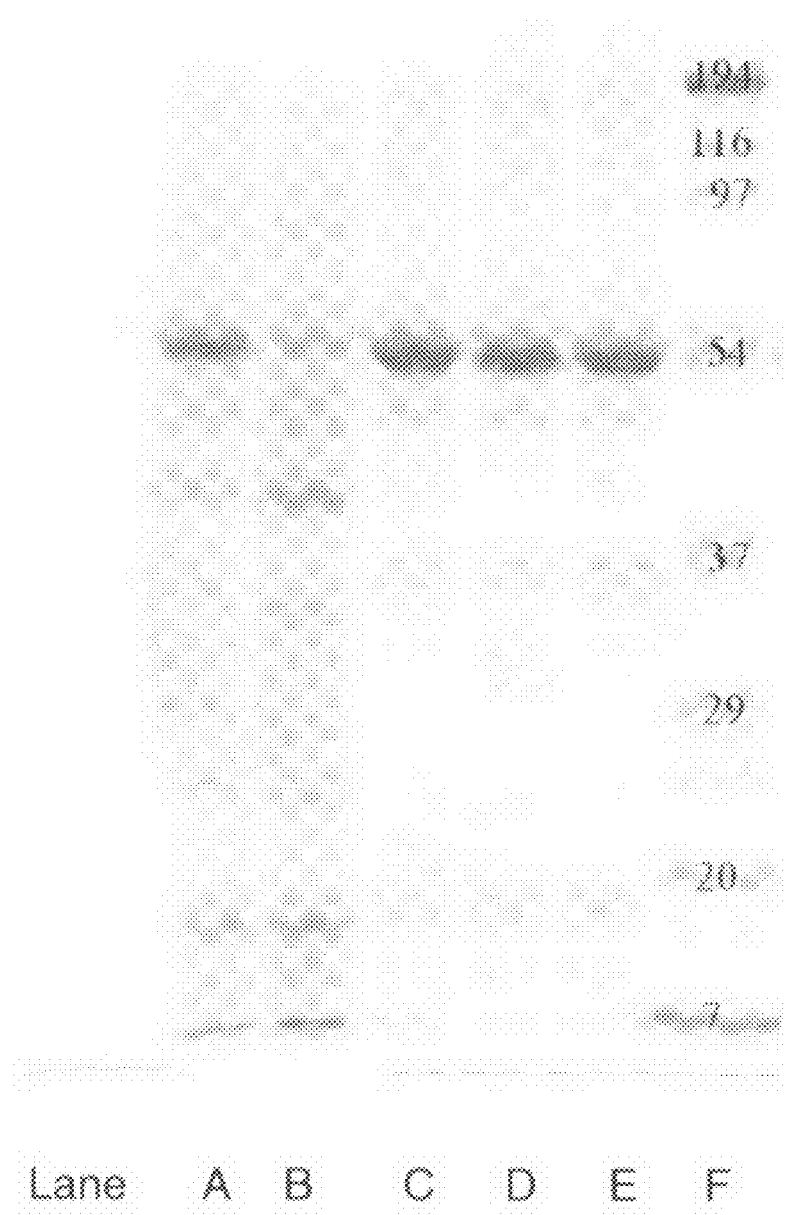

| WO | WO-03/010331 A2 | 2/2003 |
| --- | --- | --- |
| WO | WO-03018673 A1 | 3/2003 |
| WO | WO-03031500 A1 | 4/2003 |
| WO | WO-03/053383 A2 | 7/2003 |
| WO | WO-03080137 A1 | 10/2003 |
| WO | WO-2004/000880 A1 | 12/2003 |
| WO | W0-2005033316 A2 | 4/2005 |
| WO | WO-2005068087 A2 | 7/2005 |
| WO | WO-2005115306 A2 | 12/2005 |
| WO | WO-2006082251 A2 | 8/2006 |
| WO | WO-2006082253 A2 | 8/2006 |
| WO | WO-2006103215 A1 | 10/2006 |
| WO | WO-2006103225 A1 | 10/2006 |
| WO | WO-2006103230 A1 | 10/2006 |
| WO | WO-2006103251 A1 | 10/2006 |
| WO | WO-2006103252 A2 | 10/2006 |
| WO | WO-2006103253 A2 | 10/2006 |
| WO | WO-2006131555 A1 | 12/2006 |
| WO | WO-2006131564 A2 | 12/2006 |
| WO | WO-2006136607 A2 | 12/2006 |
| WO | WO-2007006765 A1 | 1/2007 |
| WO | WO-2007014897 A1 | 2/2007 |
| WO | WO-2007042487 A2 | 4/2007 |

OTHER PUBLICATIONS

Belitsky, B. R., "Physical and Enzymological Interaction of *Bacillus subtilis* Proteins Required for De Novo Pyridoxal 5' Phosphate Biosynthesis", Journal of Bacteriology, 2004, vol. 186, No. 4, pp. 1191-1196.

Wösten, H. A. B., "Hydrophobins: Multipurpose Proteins", Annu. Rev. Microbial., 2001, vol. 55, pp. 625-646.

Janssen, M.I., et al., Coating with Genetic Engineered Hydrophobin Promotes Growth of Fibroblasts on a Hydrophobic Solid, Biomaterials, 2002, vol. 23, pp. 4847-4854.

Ananichev, A.V., et al., "Immobilization of Glucose Isomerase by Adsorption on Porous Silochrome Under Vacuum", Prikladnaya Biokhimiya 1 Mikrobiologiya, 1984, vol. 20, No. 4, pp. 458-463.

Corvis, Y., et al., "Preparing catalytic surfaces for sensing applications by immobilizing enzymes via hydrophobin layers", Anal. Chem., 2005, vol. 77, pp. 1622-1630.

Scholtmeijer, K., et al., "Surface modifications created by using engineered hydrophobins", Applied and Environmental Microbiology, 2002, vol. 68, No. 3, pp. 1367-1373.

Scholtmeijer, K., et al., "Fungal hydrophobins in medical and technical applications", Applied Microbiology & Biotechnology, 2001, vol. 56, pp. 1-8.

Hektor, H. J., et al., "Hydrophobins: proteins with potential", Current Opinion in Biotechnology, 2005, vol. 16, pp. 434-439.

DeVocht, M. L., et al., "Structural and functional role of the disulfide bridges in the hydrophobin SC3", Journal of Biological Chemistry, 2000, vol. 275, No. 37, pp. 28428-28432.

Hider, G.C., "A relatively simple test for the direct determination of the cysteine content in photographic gelatin using a thiol-specific fluorogenic reagent", The Imaging Science Journal, 1997, vol. 45, pp. 162-166.

Bauer, J. A., et al., "Three-dimensional structure of YaaE from *Bacillus subtilis*, a glutaminase implicated in pyridoxal-5'-phosphate biosynthesis", Journal Of Biological Chemistry, 2004, vol. 279, No. 4, pp. 2704-2711.

Imai, Y., et al., "The Fission Yeast Mating Pheromone P-factor: its Molecular Structure, Gene Structure, and Ability to Induce Gene Expression and $G_1$ Arrest in the Mating Partner", Development, 1994, vol. 8, pp. 328-338.

Nakari-Setala, T., et al., "Expression of a Fungal Hydrophobin in the *Saccharomyces cerevisiae* Cell Wall; Effect on Cell Surface Properties and Immobilization", Applied and Environmental Microbiology, 2002, vol. 68, No. 7, pp. 3385-3391.

Linder, M., et al., "Surface Adhesion of Fusion Proteins Containing the Hydrophobins HFBI and HFBII from *Trichoderma reesei*", Protein Science, 2002, vol. 11, pp. 2257-2266.

\* cited by examiner

SEQUENCE LISTING

```
<160> NUMBER OF SEQ ID NOS: 35

<210> SEQ ID NO 1
<211> LENGTH: 405
<212> TYPE: DNA
<213> ORGANISM: Aspergillus nidulans
<220> FEATURE:
<221> NAME/KEY: CDS
<222> LOCATION: (1)..(405)
<223> OTHER INFORMATION: basf-dewA hydrophobin

<400> SEQUENCE: 1 atg cgc ttc atc gtc tct ctc ctc gcc ttc act gcc gcg gcc acc gcg       48
Met Arg Phe Ile Val Ser Leu Leu Ala Phe Thr Ala Ala Ala Thr Ala
1               5                   10                  15 acc gcc ctc ccg gcc tct gcc gca aag aac gcg aag ctg gcc acc tcg       96
Thr Ala Leu Pro Ala Ser Ala Ala Lys Asn Ala Lys Leu Ala Thr Ser
            20                  25                  30 gcg gcc ttc gcc aag cag gct gaa ggc acc acc tgc aat gtc ggc tcg      144
Ala Ala Phe Ala Lys Gln Ala Glu Gly Thr Thr Cys Asn Val Gly Ser
        35                  40                  45 atc gct tgc tgc aac tcc ccc gct gag acc aac aac gac agt ctg ttg      192
Ile Ala Cys Cys Asn Ser Pro Ala Glu Thr Asn Asn Asp Ser Leu Leu
50                  55                  60 agc ggt ctg ctc ggt gct ggc ctt ctc aac ggg ctc tcg ggc aac act      240
Ser Gly Leu Leu Gly Ala Gly Leu Leu Asn Gly Leu Ser Gly Asn Thr
65                  70                  75                  80 ggc agc gcc tgc gcc aag gcg agc ttg att gac cag ctg ggt ctg ctc      288
Gly Ser Ala Cys Ala Lys Ala Ser Leu Ile Asp Gln Leu Gly Leu Leu
                85                  90                  95 gct ctc gtc gac cac act gag gaa ggc ccc gtc tgc aag aac atc gtc      336
Ala Leu Val Asp His Thr Glu Glu Gly Pro Val Cys Lys Asn Ile Val
            100                 105                 110 gct tgc tgc cct gag gga acc acc aac tgt gtt gcc gtc gac aac gct      384
Ala Cys Cys Pro Glu Gly Thr Thr Asn Cys Val Ala Val Asp Asn Ala
        115                 120                 125 ggc gct ggt acc aag gct gag                                          405
```

Gly Ala Gly Thr Lys Ala Glu
            130                 135

<210> SEQ ID NO 2
<211> LENGTH: 135
<212> TYPE: PRT
<213> ORGANISM: Aspergillus nidulans
<220> FEATURE:
<223> OTHER INFORMATION: basf-dewA hydrophobin

<400> SEQUENCE: 2

Met Arg Phe Ile Val Ser Leu Leu Ala Phe Thr Ala Ala Thr Ala
1               5                   10                  15

Thr Ala Leu Pro Ala Ser Ala Ala Lys Asn Ala Lys Leu Ala Thr Ser
            20                  25                  30

Ala Ala Phe Ala Lys Gln Ala Glu Gly Thr Thr Cys Asn Val Gly Ser
        35                  40                  45

Ile Ala Cys Cys Asn Ser Pro Ala Glu Thr Asn Asn Asp Ser Leu Leu
    50                  55                  60

Ser Gly Leu Leu Gly Ala Gly Leu Leu Asn Gly Leu Ser Gly Asn Thr
65                  70                  75                  80

Gly Ser Ala Cys Ala Lys Ala Ser Leu Ile Asp Gln Leu Gly Leu Leu
                85                  90                  95

Ala Leu Val Asp His Thr Glu Glu Gly Pro Val Cys Lys Asn Ile Val
            100                 105                 110

Ala Cys Cys Pro Glu Gly Thr Thr Asn Cys Val Ala Val Asp Asn Ala
        115                 120                 125

Gly Ala Gly Thr Lys Ala Glu
            130                 135

<210> SEQ ID NO 3
<211> LENGTH: 471
<212> TYPE: DNA
<213> ORGANISM: Aspergillus nidulans
<220> FEATURE:
<221> NAME/KEY: CDS
<222> LOCATION: (1)..(471)
<223> OTHER INFORMATION: basf-rodA hydrophobin

<400> SEQUENCE: 3 atg aag ttc tcc att gct gcc gct gtc gtt gct ttc gcc gcc tcc gtc     48
Met Lys Phe Ser Ile Ala Ala Ala Val Val Ala Phe Ala Ala Ser Val
1               5                   10                  15 gcg gcc ctc cct cct gcc cat gat tcc cag ttc gct ggc aat ggt gtt     96
Ala Ala Leu Pro Pro Ala His Asp Ser Gln Phe Ala Gly Asn Gly Val
            20                  25                  30 ggc aac aag ggc aac agc aac gtc aag ttc cct gtc ccc gaa aac gtg    144
Gly Asn Lys Gly Asn Ser Asn Val Lys Phe Pro Val Pro Glu Asn Val
        35                  40                  45 acc gtc aag cag gcc tcc gac aag tgc ggt gac cag gcc cag ctc tct    192
Thr Val Lys Gln Ala Ser Asp Lys Cys Gly Asp Gln Ala Gln Leu Ser
    50                  55                  60 tgc tgc aac aag gcc acg tac gcc ggt gac acc aca acc gtt gat gag    240
Cys Cys Asn Lys Ala Thr Tyr Ala Gly Asp Thr Thr Thr Val Asp Glu
65                  70                  75                  80 ggt ctt ctg tct ggt gcc ctc agc ggc ctc atc ggc gcc ggg tct ggt    288
Gly Leu Leu Ser Gly Ala Leu Ser Gly Leu Ile Gly Ala Gly Ser Gly
                85                  90                  95 gcc gaa ggt ctt ggt ctc ttc gat cag tgc tcc aag ctt gat gtt gct    336
Ala Glu Gly Leu Gly Leu Phe Asp Gln Cys Ser Lys Leu Asp Val Ala
            100                 105                 110

```
gtc ctc att ggc atc caa gat ctt gtc aac cag aag tgc aag caa aac     384
Val Leu Ile Gly Ile Gln Asp Leu Val Asn Gln Lys Cys Lys Gln Asn
            115                 120                 125 att gcc tgc tgc cag aac tcc ccc tcc agc gcg gat ggc aac ctt att     432
Ile Ala Cys Cys Gln Asn Ser Pro Ser Ser Ala Asp Gly Asn Leu Ile
        130                 135                 140 ggt gtc ggt ctc cct tgc gtt gcc ctt ggc tcc atc ctc                 471
Gly Val Gly Leu Pro Cys Val Ala Leu Gly Ser Ile Leu
145                 150                 155

<210> SEQ ID NO 4
<211> LENGTH: 157
<212> TYPE: PRT
<213> ORGANISM: Aspergillus nidulans
<220> FEATURE:
<223> OTHER INFORMATION: basf-rodA hydrophobin

<400> SEQUENCE: 4

Met Lys Phe Ser Ile Ala Ala Val Val Ala Phe Ala Ala Ser Val
1               5                   10                  15

Ala Ala Leu Pro Pro Ala His Asp Ser Gln Phe Ala Gly Asn Gly Val
            20                  25                  30

Gly Asn Lys Gly Asn Ser Asn Val Lys Phe Pro Val Pro Glu Asn Val
        35                  40                  45

Thr Val Lys Gln Ala Ser Asp Lys Cys Gly Asp Gln Ala Gln Leu Ser
    50                  55                  60

Cys Cys Asn Lys Ala Thr Tyr Ala Gly Asp Thr Thr Val Asp Glu
65                  70                  75                  80

Gly Leu Leu Ser Gly Ala Leu Ser Gly Leu Ile Gly Ala Gly Ser Gly
                85                  90                  95

Ala Glu Gly Leu Gly Leu Phe Asp Gln Cys Ser Lys Leu Asp Val Ala
            100                 105                 110

Val Leu Ile Gly Ile Gln Asp Leu Val Asn Gln Lys Cys Lys Gln Asn
        115                 120                 125

Ile Ala Cys Cys Gln Asn Ser Pro Ser Ser Ala Asp Gly Asn Leu Ile
    130                 135                 140

Gly Val Gly Leu Pro Cys Val Ala Leu Gly Ser Ile Leu
145                 150                 155

<210> SEQ ID NO 5
<211> LENGTH: 336
<212> TYPE: DNA
<213> ORGANISM: Artificial Sequence
<220> FEATURE:
<221> NAME/KEY: CDS
<222> LOCATION: (1)..(336)
<223> OTHER INFORMATION: Chemically synthesized polynucleotide basf-hypA

<400> SEQUENCE: 5 atg atc tct cgc gtc ctt gtc gct gct ctc gtc gct ctc ccc gct ctt     48
Met Ile Ser Arg Val Leu Val Ala Ala Leu Val Ala Leu Pro Ala Leu
1               5                   10                  15 gtt act gca act cct gct ccc gga aag cct aaa gcc agc agt cag tgc     96
Val Thr Ala Thr Pro Ala Pro Gly Lys Pro Lys Ala Ser Ser Gln Cys
            20                  25                  30 gac gtc ggt gaa atc cat tgc tgt gac act cag cag act ccc gac cac    144
Asp Val Gly Glu Ile His Cys Cys Asp Thr Gln Gln Thr Pro Asp His
        35                  40                  45 acc agc gcc gcc gcg tct ggt ttg ctt ggt gtt ccc atc aac ctt ggt    192
Thr Ser Ala Ala Ala Ser Gly Leu Leu Gly Val Pro Ile Asn Leu Gly
```

```
                50                  55                  60
gct ttc ctc ggt ttc gac tgt acc ccc att tcc gtc ctt ggc gtc ggt    240
Ala Phe Leu Gly Phe Asp Cys Thr Pro Ile Ser Val Leu Gly Val Gly
 65                  70                  75                  80 ggc aac aac tgt gct gct cag cct gtc tgc tgc aca gga aat caa ttc    288
Gly Asn Asn Cys Ala Ala Gln Pro Val Cys Cys Thr Gly Asn Gln Phe
                 85                  90                  95 acc gca ttg att aac gct ctt gac tgc tct cct gtc aat gtc aac ctc    336
Thr Ala Leu Ile Asn Ala Leu Asp Cys Ser Pro Val Asn Val Asn Leu
                100                 105                 110

<210> SEQ ID NO 6
<211> LENGTH: 112
<212> TYPE: PRT
<213> ORGANISM: Artificial Sequence
<220> FEATURE:
<223> OTHER INFORMATION: basf-hypA from chemically synthesized
      polynucleotide

<400> SEQUENCE: 6

Met Ile Ser Arg Val Leu Val Ala Ala Leu Val Ala Leu Pro Ala Leu
 1               5                  10                  15

Val Thr Ala Thr Pro Ala Pro Gly Lys Pro Lys Ala Ser Ser Gln Cys
                 20                  25                  30

Asp Val Gly Glu Ile His Cys Cys Asp Thr Gln Gln Thr Pro Asp His
             35                  40                  45

Thr Ser Ala Ala Ala Ser Gly Leu Leu Gly Val Pro Ile Asn Leu Gly
         50                  55                  60

Ala Phe Leu Gly Phe Asp Cys Thr Pro Ile Ser Val Leu Gly Val Gly
 65                  70                  75                  80

Gly Asn Asn Cys Ala Ala Gln Pro Val Cys Cys Thr Gly Asn Gln Phe
 85                  90                  95

Thr Ala Leu Ile Asn Ala Leu Asp Cys Ser Pro Val Asn Val Asn Leu
                100                 105                 110

<210> SEQ ID NO 7
<211> LENGTH: 357
<212> TYPE: DNA
<213> ORGANISM: Artificial Sequence
<220> FEATURE:
<221> NAME/KEY: CDS
<222> LOCATION: (1)..(357)
<223> OTHER INFORMATION: chemically synthesized polynucleotide basf-hypB

<400> SEQUENCE: 7 atg gtc agc acg ttc atc act gtc gca aag acc ctt ctc gtc gcg ctc    48
Met Val Ser Thr Phe Ile Thr Val Ala Lys Thr Leu Leu Val Ala Leu
 1               5                  10                  15 ctc ttc gtc aat atc aat atc gtc gtt ggt act gca act acc ggc aag    96
Leu Phe Val Asn Ile Asn Ile Val Val Gly Thr Ala Thr Thr Gly Lys
                 20                  25                  30 cat tgt agc acc ggt cct atc gag tgc tgc aag cag gtc atg gat tct    144
His Cys Ser Thr Gly Pro Ile Glu Cys Cys Lys Gln Val Met Asp Ser
             35                  40                  45 aag agc cct cag gct acg gag ctt ctt acg aag aat ggc ctt ggc ctg    192
Lys Ser Pro Gln Ala Thr Glu Leu Leu Thr Lys Asn Gly Leu Gly Leu
         50                  55                  60 ggt gtc ctt gct ggc gtg aag ggt ctt gtt ggc gcg aat tgc agc cct    240
Gly Val Leu Ala Gly Val Lys Gly Leu Val Gly Ala Asn Cys Ser Pro
 65                  70                  75                  80 atc acg gca att ggt att ggc tcc ggc agc caa tgc tct ggc cag acc    288
```

```
Ile Thr Ala Ile Gly Ile Gly Ser Gly Ser Gln Cys Ser Gly Gln Thr
                85                  90                  95 gtt tgc tgc cag aat aat aat ttc aac ggt gtt gtc gct att ggt tgc    336
Val Cys Cys Gln Asn Asn Asn Phe Asn Gly Val Val Ala Ile Gly Cys
            100                 105                 110 act ccc att aat gcc aat gtg                                        357
Thr Pro Ile Asn Ala Asn Val
        115

<210> SEQ ID NO 8
<211> LENGTH: 119
<212> TYPE: PRT
<213> ORGANISM: Artificial Sequence
<220> FEATURE:
<223> OTHER INFORMATION: basf-hypB from chemically synthesized
      polynucleotide

<400> SEQUENCE: 8

Met Val Ser Thr Phe Ile Thr Val Ala Lys Thr Leu Leu Val Ala Leu
1               5                   10                  15

Leu Phe Val Asn Ile Asn Ile Val Val Gly Thr Ala Thr Thr Gly Lys
            20                  25                  30

His Cys Ser Thr Gly Pro Ile Glu Cys Cys Lys Gln Val Met Asp Ser
        35                  40                  45

Lys Ser Pro Gln Ala Thr Glu Leu Leu Thr Lys Asn Gly Leu Gly Leu
    50                  55                  60

Gly Val Leu Ala Gly Val Lys Gly Leu Val Gly Ala Asn Cys Ser Pro
65                  70                  75                  80

Ile Thr Ala Ile Gly Ile Gly Ser Gly Ser Gln Cys Ser Gly Gln Thr
                85                  90                  95

Val Cys Cys Gln Asn Asn Asn Phe Asn Gly Val Val Ala Ile Gly Cys
            100                 105                 110

Thr Pro Ile Asn Ala Asn Val
        115

<210> SEQ ID NO 9
<211> LENGTH: 408
<212> TYPE: DNA
<213> ORGANISM: Schyzophyllum commune
<220> FEATURE:
<221> NAME/KEY: CDS
<222> LOCATION: (1)..(408)
<223> OTHER INFORMATION: basf-sc3 hydrophobin, cDNA template

<400> SEQUENCE: 9 atg ttc gcc cgt ctc ccc gtc gtg ttc ctc tac gcc ttc gtc gcg ttc    48
Met Phe Ala Arg Leu Pro Val Val Phe Leu Tyr Ala Phe Val Ala Phe
1               5                   10                  15 ggc gcc ctc gtc gct gcc ctc cca ggt ggc cac ccg ggc acg acc acg    96
Gly Ala Leu Val Ala Ala Leu Pro Gly Gly His Pro Gly Thr Thr Thr
            20                  25                  30 ccg ccg gtt acg acg acg gtg acg gtg acc acg ccg ccc tcg acg acg    144
Pro Pro Val Thr Thr Thr Val Thr Val Thr Thr Pro Pro Ser Thr Thr
        35                  40                  45 acc atc gcc gcc ggt ggc acg tgt act acg ggg tcg ctc tct tgc tgc    192
Thr Ile Ala Ala Gly Gly Thr Cys Thr Thr Gly Ser Leu Ser Cys Cys
    50                  55                  60 aac cag gtt caa tcg gcg agc agc agc cct gtt acc gcc ctc ctc ggc    240
Asn Gln Val Gln Ser Ala Ser Ser Ser Pro Val Thr Ala Leu Leu Gly
65                  70                  75                  80 ctg ctc ggc att gtc ctc agc gac ctc aac gtt ctc gtt ggc atc agc    288
Leu Leu Gly Ile Val Leu Ser Asp Leu Asn Val Leu Val Gly Ile Ser
```

```
Leu Leu Gly Ile Val Leu Ser Asp Leu Asn Val Leu Val Gly Ile Ser
            85                  90                  95 tgc tct ccc ctc act gtc atc ggt gtc gga ggc agc ggc tgt tcg gcg      336
Cys Ser Pro Leu Thr Val Ile Gly Val Gly Gly Ser Gly Cys Ser Ala
            100                 105                 110 cag acc gtc tgc tgc gaa aac acc caa ttc aac ggg ctg atc aac atc      384
Gln Thr Val Cys Cys Glu Asn Thr Gln Phe Asn Gly Leu Ile Asn Ile
            115                 120                 125 ggt tgc acc ccc atc aac atc ctc                                      408
Gly Cys Thr Pro Ile Asn Ile Leu
            130             135

<210> SEQ ID NO 10
<211> LENGTH: 136
<212> TYPE: PRT
<213> ORGANISM: Schyzophyllum commune
<220> FEATURE:
<223> OTHER INFORMATION: basf-sc3 hydrophobin, cDNA

<400> SEQUENCE: 10

Met Phe Ala Arg Leu Pro Val Val Phe Leu Tyr Ala Phe Val Ala Phe
1               5                   10                  15

Gly Ala Leu Val Ala Ala Leu Pro Gly Gly His Pro Gly Thr Thr Thr
            20                  25                  30

Pro Pro Val Thr Thr Val Thr Val Thr Thr Pro Pro Ser Thr Thr Thr
            35                  40                  45

Thr Ile Ala Ala Gly Gly Thr Cys Thr Thr Gly Ser Leu Ser Cys Cys
    50                  55                  60

Asn Gln Val Gln Ser Ala Ser Ser Ser Pro Val Thr Ala Leu Leu Gly
65                  70                  75                  80

Leu Leu Gly Ile Val Leu Ser Asp Leu Asn Val Leu Val Gly Ile Ser
            85                  90                  95

Cys Ser Pro Leu Thr Val Ile Gly Val Gly Gly Ser Gly Cys Ser Ala
            100                 105                 110

Gln Thr Val Cys Cys Glu Asn Thr Gln Phe Asn Gly Leu Ile Asn Ile
            115                 120                 125

Gly Cys Thr Pro Ile Asn Ile Leu
            130             135

<210> SEQ ID NO 11
<211> LENGTH: 483
<212> TYPE: DNA
<213> ORGANISM: Artificial Sequence
<220> FEATURE:
<221> NAME/KEY: CDS
<222> LOCATION: (1)..(483)
<223> OTHER INFORMATION: chemically synthesized polynucleotide
      basf-BASF1

<400> SEQUENCE: 11 atg aag ttc tcc gtc tcc gcc gcc gtc ctc gcc ttc gcc gcc tcc gtc      48
Met Lys Phe Ser Val Ser Ala Ala Val Leu Ala Phe Ala Ala Ser Val
1               5                   10                  15 gcc gcc ctc cct cag cac gac tcc gcc gcc ggc aac ggc aac ggc gtc      96
Ala Ala Leu Pro Gln His Asp Ser Ala Ala Gly Asn Gly Asn Gly Val
            20                  25                  30 ggc aac aag ttc cct gtc cct gac gac gtc acc gtc aag cag gcc acc      144
Gly Asn Lys Phe Pro Val Pro Asp Asp Val Thr Val Lys Gln Ala Thr
            35                  40                  45 gac aag tgc ggc gac cag gcc cag ctc tcc tgc tgc aac aag gcc acc      192
Asp Lys Cys Gly Asp Gln Ala Gln Leu Ser Cys Cys Asn Lys Ala Thr
```

```
             50                  55                  60
tac gcc ggc gac gtc ctc acc gac atc gac gag ggc atc ctc gcc ggc     240
Tyr Ala Gly Asp Val Leu Thr Asp Ile Asp Glu Gly Ile Leu Ala Gly
 65                  70                  75                  80 ctc ctc aag aac ctc atc ggc ggc ggc tcc ggc tcc gag ggc ctc ggc     288
Leu Leu Lys Asn Leu Ile Gly Gly Gly Ser Gly Ser Glu Gly Leu Gly
                 85                  90                  95 ctc ttc gac cag tgc gtc aag ctc gac ctc cag atc tcc gtc atc ggc     336
Leu Phe Asp Gln Cys Val Lys Leu Asp Leu Gln Ile Ser Val Ile Gly
            100                 105                 110 atc cct atc cag gac ctc ctc aac cag gtc aac aag cag tgc aag cag     384
Ile Pro Ile Gln Asp Leu Leu Asn Gln Val Asn Lys Gln Cys Lys Gln
        115                 120                 125 aac atc gcc tgc tgc cag aac tcc cct tcc gac gcc acc ggc tcc ctc     432
Asn Ile Ala Cys Cys Gln Asn Ser Pro Ser Asp Ala Thr Gly Ser Leu
    130                 135                 140 gtc aac ctc ggc ctc ggc aac cct tgc atc cct gtc tcc ctc ctc cat     480
Val Asn Leu Gly Leu Gly Asn Pro Cys Ile Pro Val Ser Leu Leu His
145                 150                 155                 160 atg                                                                 483
Met
```

<210> SEQ ID NO 12
<211> LENGTH: 161
<212> TYPE: PRT
<213> ORGANISM: Artificial Sequence
<220> FEATURE:
<223> OTHER INFORMATION: basf-BASF1 from chemically synthesized polynucleotide

<400> SEQUENCE: 12

Met Lys Phe Ser Val Ser Ala Ala Val Leu Ala Phe Ala Ala Ser Val
1               5                   10                  15

Ala Ala Leu Pro Gln His Asp Ser Ala Ala Gly Asn Gly Asn Gly Val
            20                  25                  30

Gly Asn Lys Phe Pro Val Pro Asp Asp Val Thr Val Lys Gln Ala Thr
        35                  40                  45

Asp Lys Cys Gly Asp Gln Ala Gln Leu Ser Cys Cys Asn Lys Ala Thr
    50                  55                  60

Tyr Ala Gly Asp Val Leu Thr Asp Ile Asp Glu Gly Ile Leu Ala Gly
65                  70                  75                  80

Leu Leu Lys Asn Leu Ile Gly Gly Gly Ser Gly Ser Glu Gly Leu Gly
                85                  90                  95

Leu Phe Asp Gln Cys Val Lys Leu Asp Leu Gln Ile Ser Val Ile Gly
            100                 105                 110

Ile Pro Ile Gln Asp Leu Leu Asn Gln Val Asn Lys Gln Cys Lys Gln
        115                 120                 125

Asn Ile Ala Cys Cys Gln Asn Ser Pro Ser Asp Ala Thr Gly Ser Leu
    130                 135                 140

Val Asn Leu Gly Leu Gly Asn Pro Cys Ile Pro Val Ser Leu Leu His
145                 150                 155                 160

Met

<210> SEQ ID NO 13
<211> LENGTH: 465
<212> TYPE: DNA
<213> ORGANISM: Artificial Sequence
<220> FEATURE:
<221> NAME/KEY: CDS
<222> LOCATION: (1)..(465)
<223> OTHER INFORMATION: chemically synthesized polynucleotide basf-BASF2

<400> SEQUENCE: 13

```
atg aag ttc tcc gtc tcc gcc gcc gtc ctc gcc ttc gcc gcc tcc gtc       48
Met Lys Phe Ser Val Ser Ala Ala Val Leu Ala Phe Ala Ala Ser Val
1               5                   10                  15 gcc gcc ctc cct cag cac gac tcc gcc gcc ggc aac ggc aac ggc gtc       96
Ala Ala Leu Pro Gln His Asp Ser Ala Ala Gly Asn Gly Asn Gly Val
            20                  25                  30 ggc aac aag ttc cct gtc cct gac gac gtc acc gtc aag cag gcc acc      144
Gly Asn Lys Phe Pro Val Pro Asp Asp Val Thr Val Lys Gln Ala Thr
        35                  40                  45 gac aag tgc ggc gac cag gcc cag ctc tcc tgc tgc aac aag gcc acc      192
Asp Lys Cys Gly Asp Gln Ala Gln Leu Ser Cys Cys Asn Lys Ala Thr
    50                  55                  60 tac gcc ggc gac gtc acc gac atc gac gag ggc atc ctc gcc ggc ctc      240
Tyr Ala Gly Asp Val Thr Asp Ile Asp Glu Gly Ile Leu Ala Gly Leu
65                  70                  75                  80 ctc aag aac ctc atc ggc ggc ggc tcc ggc tcc gag ggc ctc ggc ctc      288
Leu Lys Asn Leu Ile Gly Gly Gly Ser Gly Ser Glu Gly Leu Gly Leu
                85                  90                  95 ttc gac cag tgc gtc aag ctc gac ctc cag atc tcc gtc atc ggc atc      336
Phe Asp Gln Cys Val Lys Leu Asp Leu Gln Ile Ser Val Ile Gly Ile
            100                 105                 110 cct atc cag gac ctc ctc aac cag cag tgc aag cag aac atc gcc tgc      384
Pro Ile Gln Asp Leu Leu Asn Gln Gln Cys Lys Gln Asn Ile Ala Cys
        115                 120                 125 tgc cag aac tcc cct tcc gac gcc acc ggc tcc ctc gtc aac ctc ggc      432
Cys Gln Asn Ser Pro Ser Asp Ala Thr Gly Ser Leu Val Asn Leu Gly
    130                 135                 140 aac cct tgc atc cct gtc tcc ctc ctc cat atg                          465
Asn Pro Cys Ile Pro Val Ser Leu Leu His Met
145                 150                 155
```

<210> SEQ ID NO 14
<211> LENGTH: 155
<212> TYPE: PRT
<213> ORGANISM: Artificial Sequence
<220> FEATURE:
<223> OTHER INFORMATION: basf-BASF2 from chemically synthesized polynucleotide

<400> SEQUENCE: 14

```
Met Lys Phe Ser Val Ser Ala Ala Val Leu Ala Phe Ala Ala Ser Val
1               5                   10                  15

Ala Ala Leu Pro Gln His Asp Ser Ala Ala Gly Asn Gly Asn Gly Val
            20                  25                  30

Gly Asn Lys Phe Pro Val Pro Asp Asp Val Thr Val Lys Gln Ala Thr
        35                  40                  45

Asp Lys Cys Gly Asp Gln Ala Gln Leu Ser Cys Cys Asn Lys Ala Thr
    50                  55                  60

Tyr Ala Gly Asp Val Thr Asp Ile Asp Glu Gly Ile Leu Ala Gly Leu
65                  70                  75                  80

Leu Lys Asn Leu Ile Gly Gly Gly Ser Gly Ser Glu Gly Leu Gly Leu
                85                  90                  95

Phe Asp Gln Cys Val Lys Leu Asp Leu Gln Ile Ser Val Ile Gly Ile
            100                 105                 110

Pro Ile Gln Asp Leu Leu Asn Gln Gln Cys Lys Gln Asn Ile Ala Cys
```

-continued

```
              115                 120                 125
Cys Gln Asn Ser Pro Ser Asp Ala Thr Gly Ser Leu Val Asn Leu Gly
        130                 135                 140

Asn Pro Cys Ile Pro Val Ser Leu Leu His Met
145                 150                 155

<210> SEQ ID NO 15
<211> LENGTH: 882
<212> TYPE: DNA
<213> ORGANISM: Bacillus subtilis
<220> FEATURE:
<221> NAME/KEY: CDS
<222> LOCATION: (1)..(882)
<223> OTHER INFORMATION: basf-yaad: yaaD

<400> SEQUENCE: 15 atg gct caa aca ggt act gaa cgt gta aaa cgc gga atg gca gaa atg        48
Met Ala Gln Thr Gly Thr Glu Arg Val Lys Arg Gly Met Ala Glu Met
1               5                  10                  15 caa aaa ggc ggc gtc atc atg gac gtc atc aat gcg gaa caa gcg aaa        96
Gln Lys Gly Gly Val Ile Met Asp Val Ile Asn Ala Glu Gln Ala Lys
                20                  25                  30 atc gct gaa gaa gct gga gct gtc gct gta atg gcg cta gaa cgt gtg       144
Ile Ala Glu Glu Ala Gly Ala Val Ala Val Met Ala Leu Glu Arg Val
            35                  40                  45 cca gca gat att cgc gcg gct gga gga gtt gcc cgt atg gct gac cct       192
Pro Ala Asp Ile Arg Ala Ala Gly Gly Val Ala Arg Met Ala Asp Pro
        50                  55                  60 aca atc gtg gaa gaa gta atg aat gca gta tct atc ccg gta atg gca       240
Thr Ile Val Glu Glu Val Met Asn Ala Val Ser Ile Pro Val Met Ala
65                  70                  75                  80 aaa gcg cgt atc gga cat att gtt gaa gcg cgt gtg ctt gaa gct atg       288
Lys Ala Arg Ile Gly His Ile Val Glu Ala Arg Val Leu Glu Ala Met
                85                  90                  95 ggt gtt gac tat att gat gaa agt gaa gtt ctg acg ccg gct gac gaa       336
Gly Val Asp Tyr Ile Asp Glu Ser Glu Val Leu Thr Pro Ala Asp Glu
                100                 105                 110 gaa ttt cat tta aat aaa aat gaa tac aca gtt cct ttt gtc tgt ggc       384
Glu Phe His Leu Asn Lys Asn Glu Tyr Thr Val Pro Phe Val Cys Gly
            115                 120                 125 tgc cgt gat ctt ggt gaa gca aca cgc cgt att gcg gaa ggt gct tct       432
Cys Arg Asp Leu Gly Glu Ala Thr Arg Arg Ile Ala Glu Gly Ala Ser
        130                 135                 140 atg ctt cgc aca aaa ggt gag cct gga aca ggt aat att gtt gag gct       480
Met Leu Arg Thr Lys Gly Glu Pro Gly Thr Gly Asn Ile Val Glu Ala
145                 150                 155                 160 gtt cgc cat atg cgt aaa gtt aac gct caa gtg cgc aaa gta gtt gcg       528
Val Arg His Met Arg Lys Val Asn Ala Gln Val Arg Lys Val Val Ala
                165                 170                 175 atg agt gag gat gag cta atg aca gaa gcg aaa aac cta ggt gct cct       576
Met Ser Glu Asp Glu Leu Met Thr Glu Ala Lys Asn Leu Gly Ala Pro
                180                 185                 190 tac gag ctt ctt ctt caa att aaa aaa gac ggc aag ctt cct gtc gtt       624
Tyr Glu Leu Leu Leu Gln Ile Lys Lys Asp Gly Lys Leu Pro Val Val
            195                 200                 205 aac ttt gcc gct ggc ggc gta gca act cca gct gat gct gct ctc atg       672
Asn Phe Ala Ala Gly Gly Val Ala Thr Pro Ala Asp Ala Ala Leu Met
        210                 215                 220 atg cag ctt ggt gct gac gga gta ttt gtt ggt tct ggt att ttt aaa       720
Met Gln Leu Gly Ala Asp Gly Val Phe Val Gly Ser Gly Ile Phe Lys
225                 230                 235                 240
```

```
tca gac aac cct gct aaa ttt gcg aaa gca att gtg gaa gca aca act    768
Ser Asp Asn Pro Ala Lys Phe Ala Lys Ala Ile Val Glu Ala Thr Thr
            245                 250                 255 cac ttt act gat tac aaa tta atc gct gag ttg tca aaa gag ctt ggt    816
His Phe Thr Asp Tyr Lys Leu Ile Ala Glu Leu Ser Lys Glu Leu Gly
            260                 265                 270 act gca atg aaa ggg att gaa atc tca aac tta ctt cca gaa cag cgt    864
Thr Ala Met Lys Gly Ile Glu Ile Ser Asn Leu Leu Pro Glu Gln Arg
            275                 280                 285 atg caa gaa cgc ggc tgg                                            882
Met Gln Glu Arg Gly Trp
    290
```

<210> SEQ ID NO 16
<211> LENGTH: 294
<212> TYPE: PRT
<213> ORGANISM: Bacillus subtilis
<220> FEATURE:
<223> OTHER INFORMATION: basf-yaad: yaaD

<400> SEQUENCE: 16

```
Met Ala Gln Thr Gly Thr Glu Arg Val Lys Arg Gly Met Ala Glu Met
1               5                   10                  15

Gln Lys Gly Gly Val Ile Met Asp Val Ile Asn Ala Glu Gln Ala Lys
            20                  25                  30

Ile Ala Glu Glu Ala Gly Ala Val Ala Val Met Ala Leu Glu Arg Val
        35                  40                  45

Pro Ala Asp Ile Arg Ala Ala Gly Gly Val Ala Arg Met Ala Asp Pro
    50                  55                  60

Thr Ile Val Glu Glu Val Met Asn Ala Val Ser Ile Pro Val Met Ala
65                  70                  75                  80

Lys Ala Arg Ile Gly His Ile Val Glu Ala Arg Val Leu Glu Ala Met
                85                  90                  95

Gly Val Asp Tyr Ile Asp Glu Ser Glu Val Leu Thr Pro Ala Asp Glu
            100                 105                 110

Glu Phe His Leu Asn Lys Asn Glu Tyr Thr Val Pro Phe Val Cys Gly
        115                 120                 125

Cys Arg Asp Leu Gly Glu Ala Thr Arg Arg Ile Ala Glu Gly Ala Ser
    130                 135                 140

Met Leu Arg Thr Lys Gly Glu Pro Gly Thr Gly Asn Ile Val Glu Ala
145                 150                 155                 160

Val Arg His Met Arg Lys Val Asn Ala Gln Val Arg Lys Val Val Ala
                165                 170                 175

Met Ser Glu Asp Glu Leu Met Thr Glu Ala Lys Asn Leu Gly Ala Pro
            180                 185                 190

Tyr Glu Leu Leu Leu Gln Ile Lys Lys Asp Gly Lys Leu Pro Val Val
        195                 200                 205

Asn Phe Ala Ala Gly Gly Val Ala Thr Pro Ala Asp Ala Ala Leu Met
    210                 215                 220

Met Gln Leu Gly Ala Asp Gly Val Phe Val Gly Ser Gly Ile Phe Lys
225                 230                 235                 240

Ser Asp Asn Pro Ala Lys Phe Ala Lys Ala Ile Val Glu Ala Thr Thr
                245                 250                 255

His Phe Thr Asp Tyr Lys Leu Ile Ala Glu Leu Ser Lys Glu Leu Gly
            260                 265                 270

Thr Ala Met Lys Gly Ile Glu Ile Ser Asn Leu Leu Pro Glu Gln Arg
```

Met Gln Glu Arg Gly Trp
    290

<210> SEQ ID NO 17
<211> LENGTH: 591
<212> TYPE: DNA
<213> ORGANISM: Bacillus subtilis
<220> FEATURE:
<221> NAME/KEY: CDS
<222> LOCATION: (1)..(591)
<223> OTHER INFORMATION: basf-yaae: yaaE with Gly insert at position 2

<400> SEQUENCE: 17

```
atg gga tta aca ata ggt gta cta gga ctt caa gga gca gtt aga gag      48
Met Gly Leu Thr Ile Gly Val Leu Gly Leu Gln Gly Ala Val Arg Glu
1               5                   10                  15 cac atc cat gcg att gaa gca tgc ggc gcg gct ggt ctt gtc gta aaa      96
His Ile His Ala Ile Glu Ala Cys Gly Ala Ala Gly Leu Val Val Lys
            20                  25                  30 cgt ccg gag cag ctg aac gaa gtt gac ggg ttg att ttg ccg ggc ggt     144
Arg Pro Glu Gln Leu Asn Glu Val Asp Gly Leu Ile Leu Pro Gly Gly
        35                  40                  45 gag agc acg acg atg cgc cgt ttg atc gat acg tat caa ttc atg gag     192
Glu Ser Thr Thr Met Arg Arg Leu Ile Asp Thr Tyr Gln Phe Met Glu
    50                  55                  60 ccg ctt cgt gaa ttc gct gct cag ggc aaa ccg atg ttt gga aca tgt     240
Pro Leu Arg Glu Phe Ala Ala Gln Gly Lys Pro Met Phe Gly Thr Cys
65                  70                  75                  80 gcc gga tta att ata tta gca aaa gaa att gcc ggt tca gat aat cct     288
Ala Gly Leu Ile Ile Leu Ala Lys Glu Ile Ala Gly Ser Asp Asn Pro
                85                  90                  95 cat tta ggt ctt ctg aat gtg gtt gta gaa cgt aat tca ttt ggc cgg     336
His Leu Gly Leu Leu Asn Val Val Val Glu Arg Asn Ser Phe Gly Arg
            100                 105                 110 cag gtt gac agc ttt gaa gct gat tta aca att aaa ggc ttg gac gag     384
Gln Val Asp Ser Phe Glu Ala Asp Leu Thr Ile Lys Gly Leu Asp Glu
        115                 120                 125 cct ttt act ggg gta ttc atc cgt gct ccg cat att tta gaa gct ggt     432
Pro Phe Thr Gly Val Phe Ile Arg Ala Pro His Ile Leu Glu Ala Gly
    130                 135                 140 gaa aat gtt gaa gtt cta tcg gag cat aat ggt cgt att gta gcc gcg     480
Glu Asn Val Glu Val Leu Ser Glu His Asn Gly Arg Ile Val Ala Ala
145                 150                 155                 160 aaa cag ggg caa ttc ctt ggc tgc tca ttc cat ccg gag ctg aca gaa     528
Lys Gln Gly Gln Phe Leu Gly Cys Ser Phe His Pro Glu Leu Thr Glu
                165                 170                 175 gat cac cga gtg acg cag ctg ttt gtt gaa atg gtt gag gaa tat aag     576
Asp His Arg Val Thr Gln Leu Phe Val Glu Met Val Glu Glu Tyr Lys
            180                 185                 190 caa aag gca ctt gta                                                  591
Gln Lys Ala Leu Val
        195
```

<210> SEQ ID NO 18
<211> LENGTH: 197
<212> TYPE: PRT
<213> ORGANISM: Bacillus subtilis
<220> FEATURE:
<223> OTHER INFORMATION: basf-yaae: yaaE with Gly insert at position 2

<400> SEQUENCE: 18

```
Met Gly Leu Thr Ile Gly Val Leu Gly Leu Gln Gly Ala Val Arg Glu
1               5                   10                  15

His Ile His Ala Ile Glu Ala Cys Gly Ala Ala Gly Leu Val Val Lys
            20                  25                  30

Arg Pro Glu Gln Leu Asn Glu Val Asp Gly Leu Ile Leu Pro Gly Gly
        35                  40                  45

Glu Ser Thr Thr Met Arg Arg Leu Ile Asp Thr Tyr Gln Phe Met Glu
    50                  55                  60

Pro Leu Arg Glu Phe Ala Ala Gln Gly Lys Pro Met Phe Gly Thr Cys
65                  70                  75                  80

Ala Gly Leu Ile Ile Leu Ala Lys Glu Ile Ala Gly Ser Asp Asn Pro
                85                  90                  95

His Leu Gly Leu Leu Asn Val Val Val Glu Arg Asn Ser Phe Gly Arg
            100                 105                 110

Gln Val Asp Ser Phe Glu Ala Asp Leu Thr Ile Lys Gly Leu Asp Glu
        115                 120                 125

Pro Phe Thr Gly Val Phe Ile Arg Ala Pro His Ile Leu Glu Ala Gly
    130                 135                 140

Glu Asn Val Glu Val Leu Ser Glu His Asn Gly Arg Ile Val Ala Ala
145                 150                 155                 160

Lys Gln Gly Gln Phe Leu Gly Cys Ser Phe His Pro Glu Leu Thr Glu
                165                 170                 175

Asp His Arg Val Thr Gln Leu Phe Val Glu Met Val Glu Glu Tyr Lys
            180                 185                 190

Gln Lys Ala Leu Val
        195

<210> SEQ ID NO 19
<211> LENGTH: 1329
<212> TYPE: DNA
<213> ORGANISM: Artificial Sequence
<220> FEATURE:
<221> NAME/KEY: CDS
<222> LOCATION: (1)..(1329)
<223> OTHER INFORMATION: basf-yaaD-Xa-dewA-his: fusion of Bacillus
      subtilis yaaD and N-terminal factor Xa proteinase cleavage site
      and Aspergillus nidulans hydrophobin dewA and his6

<400> SEQUENCE: 19 atg gct caa aca ggt act gaa cgt gta aaa cgc gga atg gca gaa atg        48
Met Ala Gln Thr Gly Thr Glu Arg Val Lys Arg Gly Met Ala Glu Met
1               5                   10                  15 caa aaa ggc ggc gtc atc atg gac gtc atc aat gcg gaa caa gcg aaa        96
Gln Lys Gly Gly Val Ile Met Asp Val Ile Asn Ala Glu Gln Ala Lys
            20                  25                  30 atc gct gaa gaa gct gga gct gtc gct gta atg gcg cta gaa cgt gtg       144
Ile Ala Glu Glu Ala Gly Ala Val Ala Val Met Ala Leu Glu Arg Val
        35                  40                  45 cca gca gat att cgc gcg gct gga gga gtt gcc cgt atg gct gac cct       192
Pro Ala Asp Ile Arg Ala Ala Gly Gly Val Ala Arg Met Ala Asp Pro
    50                  55                  60 aca atc gtg gaa gaa gta atg aat gca gta tct atc ccg gta atg gca       240
Thr Ile Val Glu Glu Val Met Asn Ala Val Ser Ile Pro Val Met Ala
65                  70                  75                  80 aaa gcg cgt atc gga cat att gtt gaa gcg cgt gtg ctt gaa gct atg       288
Lys Ala Arg Ile Gly His Ile Val Glu Ala Arg Val Leu Glu Ala Met
                85                  90                  95 ggt gtt gac tat att gat gaa agt gaa gtt ctg acg ccg gct gac gaa       336
Gly Val Asp Tyr Ile Asp Glu Ser Glu Val Leu Thr Pro Ala Asp Glu
```

-continued

```
                100               105               110
gaa ttt cat tta aat aaa aat gaa tac aca gtt cct ttt gtc tgt ggc      384
Glu Phe His Leu Asn Lys Asn Glu Tyr Thr Val Pro Phe Val Cys Gly
        115               120               125 tgc cgt gat ctt ggt gaa gca aca cgt att gcg gaa ggt gct tct          432
Cys Arg Asp Leu Gly Glu Ala Thr Arg Arg Ile Ala Glu Gly Ala Ser
130               135               140 atg ctt cgc aca aaa ggt gag cct gga aca ggt aat att gtt gag gct      480
Met Leu Arg Thr Lys Gly Glu Pro Gly Thr Gly Asn Ile Val Glu Ala
145               150               155               160 gtt cgc cat atg cgt aaa gtt aac gct caa gtg cgc aaa gta gtt gcg      528
Val Arg His Met Arg Lys Val Asn Ala Gln Val Arg Lys Val Val Ala
                165               170               175 atg agt gag gat gag cta atg aca gaa gcg aaa aac cta ggt gct cct      576
Met Ser Glu Asp Glu Leu Met Thr Glu Ala Lys Asn Leu Gly Ala Pro
            180               185               190 tac gag ctt ctt ctt caa att aaa aaa gac ggc aag ctt cct gtc gtt      624
Tyr Glu Leu Leu Leu Gln Ile Lys Lys Asp Gly Lys Leu Pro Val Val
        195               200               205 aac ttt gcc gct ggc ggc gta gca act cca gct gat gct gct ctc atg      672
Asn Phe Ala Ala Gly Gly Val Ala Thr Pro Ala Asp Ala Ala Leu Met
    210               215               220 atg cag ctt ggt gct gac gga gta ttt gtt ggt tct ggt att ttt aaa      720
Met Gln Leu Gly Ala Asp Gly Val Phe Val Gly Ser Gly Ile Phe Lys
225               230               235               240 tca gac aac cct gct aaa ttt gcg aaa gca att gtg gaa gca aca act      768
Ser Asp Asn Pro Ala Lys Phe Ala Lys Ala Ile Val Glu Ala Thr Thr
                245               250               255 cac ttt act gat tac aaa tta atc gct gag ttg tca aaa gag ctt ggt      816
His Phe Thr Asp Tyr Lys Leu Ile Ala Glu Leu Ser Lys Glu Leu Gly
            260               265               270 act gca atg aaa ggg att gaa atc tca aac tta ctt cca gaa cag cgt      864
Thr Ala Met Lys Gly Ile Glu Ile Ser Asn Leu Leu Pro Glu Gln Arg
        275               280               285 atg caa gaa cgc ggc tgg aga tcc att gaa ggc cgc atg cgc ttc atc      912
Met Gln Glu Arg Gly Trp Arg Ser Ile Glu Gly Arg Met Arg Phe Ile
    290               295               300 gtc tct ctc ctc gcc ttc act gcc gcg gcc acc gcg acc gcc ctc ccg      960
Val Ser Leu Leu Ala Phe Thr Ala Ala Ala Thr Ala Thr Ala Leu Pro
305               310               315               320 gcc tct gcc gca aag aac gcg aag ctg gcc acc tcg gcg gcc ttc gcc     1008
Ala Ser Ala Ala Lys Asn Ala Lys Leu Ala Thr Ser Ala Ala Phe Ala
                325               330               335 aag cag gct gaa ggc acc acc tgc aat gtc ggc tcg atc gct tgc tgc     1056
Lys Gln Ala Glu Gly Thr Thr Cys Asn Val Gly Ser Ile Ala Cys Cys
            340               345               350 aac tcc ccc gct gag acc aac aac gac agt ctg ttg agc ggt ctg ctc     1104
Asn Ser Pro Ala Glu Thr Asn Asn Asp Ser Leu Leu Ser Gly Leu Leu
        355               360               365 ggt gct ggc ctt ctc aac ggg ctc tcg ggc aac act ggc agc gcc tgc     1152
Gly Ala Gly Leu Leu Asn Gly Leu Ser Gly Asn Thr Gly Ser Ala Cys
    370               375               380 gcc aag gcg agc ttg att gac cag ctg ggt ctg ctc gct ctc gtc gac     1200
Ala Lys Ala Ser Leu Ile Asp Gln Leu Gly Leu Leu Ala Leu Val Asp
385               390               395               400 cac act gag gaa ggc ccc gtc tgc aag aac atc gtc gct tgc tgc cct     1248
His Thr Glu Glu Gly Pro Val Cys Lys Asn Ile Val Ala Cys Cys Pro
                405               410               415 gag gga acc acc aac tgt gtt gcc gtc gac aac gct ggc gct ggt acc     1296
Glu Gly Thr Thr Asn Cys Val Ala Val Asp Asn Ala Gly Ala Gly Thr
```

```
Glu Gly Thr Thr Asn Cys Val Ala Val Asp Asn Ala Gly Ala Gly Thr
            420                 425                 430 aag gct gag gga tct cat cac cat cac cat cac                                    1329
Lys Ala Glu Gly Ser His His His His His His
            435                 440
```

<210> SEQ ID NO 20
<211> LENGTH: 443
<212> TYPE: PRT
<213> ORGANISM: Artificial Sequence
<220> FEATURE:
<223> OTHER INFORMATION: basf-yaad-Xa-dewA-his: fusion of Bacillus
      subtilis yaaD and N-terminal factor Xa proteinase cleavage site
      and Aspergillus nidulans hydrophobin dewA and his6

<400> SEQUENCE: 20

```
Met Ala Gln Thr Gly Thr Glu Arg Val Lys Arg Gly Met Ala Glu Met
1               5                   10                  15

Gln Lys Gly Gly Val Ile Met Asp Val Ile Asn Ala Glu Gln Ala Lys
            20                  25                  30

Ile Ala Glu Glu Ala Gly Ala Val Ala Val Met Ala Leu Glu Arg Val
        35                  40                  45

Pro Ala Asp Ile Arg Ala Ala Gly Gly Val Ala Arg Met Ala Asp Pro
    50                  55                  60

Thr Ile Val Glu Glu Val Met Asn Ala Val Ser Ile Pro Val Met Ala
65                  70                  75                  80

Lys Ala Arg Ile Gly His Ile Val Glu Ala Arg Val Leu Glu Ala Met
                85                  90                  95

Gly Val Asp Tyr Ile Asp Glu Ser Glu Val Leu Thr Pro Ala Asp Glu
            100                 105                 110

Glu Phe His Leu Asn Lys Asn Glu Tyr Thr Val Pro Phe Val Cys Gly
        115                 120                 125

Cys Arg Asp Leu Gly Glu Ala Thr Arg Arg Ile Ala Glu Gly Ala Ser
    130                 135                 140

Met Leu Arg Thr Lys Gly Glu Pro Gly Thr Gly Asn Ile Val Glu Ala
145                 150                 155                 160

Val Arg His Met Arg Lys Val Asn Ala Gln Val Arg Lys Val Val Ala
                165                 170                 175

Met Ser Glu Asp Glu Leu Met Thr Glu Ala Lys Asn Leu Gly Ala Pro
            180                 185                 190

Tyr Glu Leu Leu Leu Gln Ile Lys Lys Asp Gly Lys Leu Pro Val Val
        195                 200                 205

Asn Phe Ala Ala Gly Gly Val Ala Thr Pro Ala Asp Ala Ala Leu Met
    210                 215                 220

Met Gln Leu Gly Ala Asp Gly Val Phe Val Gly Ser Gly Ile Phe Lys
225                 230                 235                 240

Ser Asp Asn Pro Ala Lys Phe Ala Lys Ala Ile Val Glu Ala Thr Thr
                245                 250                 255

His Phe Thr Asp Tyr Lys Leu Ile Ala Glu Leu Ser Lys Glu Leu Gly
            260                 265                 270

Thr Ala Met Lys Gly Ile Glu Ile Ser Asn Leu Leu Pro Glu Gln Arg
        275                 280                 285

Met Gln Glu Arg Gly Trp Arg Ser Ile Glu Gly Arg Met Arg Phe Ile
    290                 295                 300

Val Ser Leu Leu Ala Phe Thr Ala Ala Ala Thr Ala Thr Ala Leu Pro
305                 310                 315                 320
```

```
        Ala Ser Ala Ala Lys Asn Ala Lys Leu Ala Thr Ser Ala Ala Phe Ala
                    325                 330                 335

Lys Gln Ala Glu Gly Thr Thr Cys Asn Val Gly Ser Ile Ala Cys Cys
                340                 345                 350

Asn Ser Pro Ala Glu Thr Asn Asn Asp Ser Leu Leu Ser Gly Leu Leu
                    355                 360                 365

Gly Ala Gly Leu Leu Asn Gly Leu Ser Gly Asn Thr Gly Ser Ala Cys
                370                 375                 380

Ala Lys Ala Ser Leu Ile Asp Gln Leu Gly Leu Leu Ala Leu Val Asp
        385                 390                 395                 400

His Thr Glu Glu Gly Pro Val Cys Lys Asn Ile Val Ala Cys Cys Pro
                        405                 410                 415

Glu Gly Thr Thr Asn Cys Val Ala Val Asp Asn Ala Gly Ala Gly Thr
                    420                 425                 430

Lys Ala Glu Gly Ser His His His His His His
                    435                 440

<210> SEQ ID NO 21
<211> LENGTH: 1395
<212> TYPE: DNA
<213> ORGANISM: Artificial Sequence
<220> FEATURE:
<221> NAME/KEY: CDS
<222> LOCATION: (1)..(1395)
<223> OTHER INFORMATION: basf-yaaD-Xa-rodA-his: fusion of Bacillus
      subtilis yaaD and N-terminal factor Xa proteinase cleavage site
      and Aspergillus nidulans hydrophobin rodA and his6

<400> SEQUENCE: 21 atg gct caa aca ggt act gaa cgt gta aaa cgc gga atg gca gaa atg           48
Met Ala Gln Thr Gly Thr Glu Arg Val Lys Arg Gly Met Ala Glu Met
1               5                   10                  15 caa aaa ggc ggc gtc atc atg gac gtc atc aat gcg gaa caa gcg aaa           96
Gln Lys Gly Gly Val Ile Met Asp Val Ile Asn Ala Glu Gln Ala Lys
            20                  25                  30 atc gct gaa gaa gct gga gct gtc gct gta atg gcg cta gaa cgt gtg          144
Ile Ala Glu Glu Ala Gly Ala Val Ala Val Met Ala Leu Glu Arg Val
        35                  40                  45 cca gca gat att cgc gcg gct gga gga gtt gcc cgt atg gct gac cct          192
Pro Ala Asp Ile Arg Ala Ala Gly Gly Val Ala Arg Met Ala Asp Pro
    50                  55                  60 aca atc gtg gaa gaa gta atg aat gca gta tct atc ccg gta atg gca          240
Thr Ile Val Glu Glu Val Met Asn Ala Val Ser Ile Pro Val Met Ala
65                  70                  75                  80 aaa gcg cgt atc gga cat att gtt gaa gcg cgt gtg ctt gaa gct atg          288
Lys Ala Arg Ile Gly His Ile Val Glu Ala Arg Val Leu Glu Ala Met
                85                  90                  95 ggt gtt gac tat att gat gaa agt gaa gtt ctg acg ccg gct gac gaa          336
Gly Val Asp Tyr Ile Asp Glu Ser Glu Val Leu Thr Pro Ala Asp Glu
            100                 105                 110 gaa ttt cat tta aat aaa aat gaa tac aca gtt cct ttt gtc tgt ggc          384
Glu Phe His Leu Asn Lys Asn Glu Tyr Thr Val Pro Phe Val Cys Gly
        115                 120                 125 tgc cgt gat ctt ggt gaa gca aca cgc cgt att gcg gaa ggt gct tct          432
Cys Arg Asp Leu Gly Glu Ala Thr Arg Arg Ile Ala Glu Gly Ala Ser
    130                 135                 140 atg ctt cgc aca aaa ggt gag cct gga aca ggt aat att gtt gag gct          480
Met Leu Arg Thr Lys Gly Glu Pro Gly Thr Gly Asn Ile Val Glu Ala
145                 150                 155                 160 gtt cgc cat atg cgt aaa gtt aac gct caa gtg cgc aaa gta gtt gcg          528
```

```
                Val Arg His Met Arg Lys Val Asn Ala Gln Val Arg Lys Val Val Ala
                            165                 170                 175 atg agt gag gat gag cta atg aca gaa gcg aaa aac cta ggt gct cct        576
Met Ser Glu Asp Glu Leu Met Thr Glu Ala Lys Asn Leu Gly Ala Pro
            180                 185                 190 tac gag ctt ctt ctt caa att aaa aaa gac ggc aag ctt cct gtc gtt        624
Tyr Glu Leu Leu Leu Gln Ile Lys Lys Asp Gly Lys Leu Pro Val Val
            195                 200                 205 aac ttt gcc gct ggc ggc gta gca act cca gct gat gct gct ctc atg        672
Asn Phe Ala Ala Gly Gly Val Ala Thr Pro Ala Asp Ala Ala Leu Met
    210                 215                 220 atg cag ctt ggt gct gac gga gta ttt gtt ggt tct ggt att ttt aaa        720
Met Gln Leu Gly Ala Asp Gly Val Phe Val Gly Ser Gly Ile Phe Lys
225                 230                 235                 240 tca gac aac cct gct aaa ttt gcg aaa gca att gtg gaa gca aca act        768
Ser Asp Asn Pro Ala Lys Phe Ala Lys Ala Ile Val Glu Ala Thr Thr
                245                 250                 255 cac ttt act gat tac aaa tta atc gct gag ttg tca aaa gag ctt ggt        816
His Phe Thr Asp Tyr Lys Leu Ile Ala Glu Leu Ser Lys Glu Leu Gly
            260                 265                 270 act gca atg aaa ggg att gaa atc tca aac tta ctt cca gaa cag cgt        864
Thr Ala Met Lys Gly Ile Glu Ile Ser Asn Leu Leu Pro Glu Gln Arg
            275                 280                 285 atg caa gaa cgc ggc tgg aga tct att gaa ggc cgc atg aag ttc tcc        912
Met Gln Glu Arg Gly Trp Arg Ser Ile Glu Gly Arg Met Lys Phe Ser
        290                 295                 300 att gct gcc gct gtc gtt gct ttc gcc gcc tcc gtc gcg gcc ctc cct        960
Ile Ala Ala Ala Val Val Ala Phe Ala Ala Ser Val Ala Ala Leu Pro
305                 310                 315                 320 cct gcc cat gat tcc cag ttc gct ggc aat ggt gtt ggc aac aag ggc       1008
Pro Ala His Asp Ser Gln Phe Ala Gly Asn Gly Val Gly Asn Lys Gly
                325                 330                 335 aac agc aac gtc aag ttc cct gtc ccc gaa aac gtg acc gtc aag cag       1056
Asn Ser Asn Val Lys Phe Pro Val Pro Glu Asn Val Thr Val Lys Gln
            340                 345                 350 gcc tcc gac aag tgc ggt gac cag gcc cag ctc tct tgc tgc aac aag       1104
Ala Ser Asp Lys Cys Gly Asp Gln Ala Gln Leu Ser Cys Cys Asn Lys
            355                 360                 365 gcc acg tac gcc ggt gac acc aca acc gtt gat gag ggt ctt ctg tct       1152
Ala Thr Tyr Ala Gly Asp Thr Thr Thr Val Asp Glu Gly Leu Leu Ser
        370                 375                 380 ggt gcc ctc agc ggc ctc atc ggc gcc ggg tct ggt gcc gaa ggt ctt       1200
Gly Ala Leu Ser Gly Leu Ile Gly Ala Gly Ser Gly Ala Glu Gly Leu
385                 390                 395                 400 ggt ctc ttc gat cag tgc tcc aag ctt gat gtt gct gtc ctc att ggc       1248
Gly Leu Phe Asp Gln Cys Ser Lys Leu Asp Val Ala Val Leu Ile Gly
                405                 410                 415 atc caa gat ctt gtc aac cag aag tgc aag caa aac att gcc tgc tgc       1296
Ile Gln Asp Leu Val Asn Gln Lys Cys Lys Gln Asn Ile Ala Cys Cys
            420                 425                 430 cag aac tcc ccc tcc agc gcg gat ggc aac ctt att ggt gtc ggt ctc       1344
Gln Asn Ser Pro Ser Ser Ala Asp Gly Asn Leu Ile Gly Val Gly Leu
            435                 440                 445 cct tgc gtt gcc ctt ggc tcc atc ctc gga tct cat cac cat cac cat       1392
Pro Cys Val Ala Leu Gly Ser Ile Leu Gly Ser His His His His His
        450                 455                 460 cac                                                                    1395
His
465
```

<210> SEQ ID NO 22
<211> LENGTH: 465
<212> TYPE: PRT
<213> ORGANISM: Artificial Sequence
<220> FEATURE:
<223> OTHER INFORMATION: basf-yaaD-Xa-rodA-his: fusion of Bacillus
subtilis yaaD and N-terminal factor Xa proteinase cleavage site
and Aspergillus nidulans hydrophobin rodA and his6

<400> SEQUENCE: 22

```
Met Ala Gln Thr Gly Thr Glu Arg Val Lys Arg Gly Met Ala Glu Met
1               5                   10                  15

Gln Lys Gly Gly Val Ile Met Asp Val Ile Asn Ala Glu Gln Ala Lys
            20                  25                  30

Ile Ala Glu Glu Ala Gly Ala Val Ala Val Met Ala Leu Glu Arg Val
        35                  40                  45

Pro Ala Asp Ile Arg Ala Ala Gly Gly Val Ala Arg Met Ala Asp Pro
    50                  55                  60

Thr Ile Val Glu Glu Val Met Asn Ala Val Ser Ile Pro Val Met Ala
65                  70                  75                  80

Lys Ala Arg Ile Gly His Ile Val Glu Ala Arg Val Leu Glu Ala Met
                85                  90                  95

Gly Val Asp Tyr Ile Asp Glu Ser Glu Val Leu Thr Pro Ala Asp Glu
            100                 105                 110

Glu Phe His Leu Asn Lys Asn Glu Tyr Thr Val Pro Phe Val Cys Gly
        115                 120                 125

Cys Arg Asp Leu Gly Glu Ala Thr Arg Arg Ile Ala Glu Gly Ala Ser
    130                 135                 140

Met Leu Arg Thr Lys Gly Glu Pro Gly Thr Gly Asn Ile Val Glu Ala
145                 150                 155                 160

Val Arg His Met Arg Lys Val Asn Ala Gln Val Arg Lys Val Val Ala
                165                 170                 175

Met Ser Glu Asp Glu Leu Met Thr Glu Ala Lys Asn Leu Gly Ala Pro
            180                 185                 190

Tyr Glu Leu Leu Leu Gln Ile Lys Lys Asp Gly Lys Leu Pro Val Val
        195                 200                 205

Asn Phe Ala Ala Gly Gly Val Ala Thr Pro Ala Asp Ala Ala Leu Met
    210                 215                 220

Met Gln Leu Gly Ala Asp Gly Val Phe Val Gly Ser Gly Ile Phe Lys
225                 230                 235                 240

Ser Asp Asn Pro Ala Lys Phe Ala Lys Ala Ile Val Glu Ala Thr Thr
                245                 250                 255

His Phe Thr Asp Tyr Lys Leu Ile Ala Glu Leu Ser Lys Glu Leu Gly
            260                 265                 270

Thr Ala Met Lys Gly Ile Glu Ile Ser Asn Leu Leu Pro Glu Gln Arg
        275                 280                 285

Met Gln Glu Arg Gly Trp Arg Ser Ile Glu Gly Arg Met Lys Phe Ser
    290                 295                 300

Ile Ala Ala Ala Val Ala Phe Ala Ala Ser Val Ala Ala Leu Pro
305                 310                 315                 320

Pro Ala His Asp Ser Gln Phe Ala Gly Asn Gly Val Gly Asn Lys Gly
                325                 330                 335

Asn Ser Asn Val Lys Phe Pro Val Pro Glu Asn Val Thr Val Lys Gln
            340                 345                 350

Ala Ser Asp Lys Cys Gly Asp Gln Ala Gln Leu Ser Cys Cys Asn Lys
```

-continued

```
                    355                 360                 365
Ala Thr Tyr Ala Gly Asp Thr Thr Val Asp Glu Gly Leu Leu Ser
            370                 375                 380

Gly Ala Leu Ser Gly Leu Ile Gly Ala Gly Ser Gly Ala Glu Gly Leu
385                 390                 395                 400

Gly Leu Phe Asp Gln Cys Ser Lys Leu Asp Val Ala Val Leu Ile Gly
                405                 410                 415

Ile Gln Asp Leu Val Asn Gln Lys Cys Lys Gln Asn Ile Ala Cys Cys
            420                 425                 430

Gln Asn Ser Pro Ser Ser Ala Asp Gly Asn Leu Ile Gly Val Gly Leu
        435                 440                 445

Pro Cys Val Ala Leu Gly Ser Ile Leu Gly Ser His His His His
    450                 455                 460

His
465

<210> SEQ ID NO 23
<211> LENGTH: 1407
<212> TYPE: DNA
<213> ORGANISM: Artificial Sequence
<220> FEATURE:
<221> NAME/KEY: CDS
<222> LOCATION: (1)..(1407)
<223> OTHER INFORMATION: basf-yaad-Xa-BASF1-his: fusion of Bacillus
      subtilis yaaD and N-terminal factor Xa proteinase cleavage site
      and artificial hydrophobin; BASF1 BASF1 from chemically
      synthesized polynucleotide

<400> SEQUENCE: 23 atg gct caa aca ggt act gaa cgt gta aaa cgc gga atg gca gaa atg      48
Met Ala Gln Thr Gly Thr Glu Arg Val Lys Arg Gly Met Ala Glu Met
 1               5                  10                  15 caa aaa ggc ggc gtc atc atg gac gtc atc aat gcg gaa caa gcg aaa      96
Gln Lys Gly Gly Val Ile Met Asp Val Ile Asn Ala Glu Gln Ala Lys
             20                  25                  30 atc gct gaa gaa gct gga gct gtc gct gta atg gcg cta gaa cgt gtg     144
Ile Ala Glu Glu Ala Gly Ala Val Ala Val Met Ala Leu Glu Arg Val
         35                  40                  45 cca gca gat att cgc gcg gct gga gga gtt gcc cgt atg gct gac cct     192
Pro Ala Asp Ile Arg Ala Ala Gly Gly Val Ala Arg Met Ala Asp Pro
     50                  55                  60 aca atc gtg gaa gaa gta atg aat gca gta tct atc ccg gta atg gca     240
Thr Ile Val Glu Glu Val Met Asn Ala Val Ser Ile Pro Val Met Ala
 65                  70                  75                  80 aaa gcg cgt atc gga cat att gtt gaa gcg cgt gtg ctt gaa gct atg     288
Lys Ala Arg Ile Gly His Ile Val Glu Ala Arg Val Leu Glu Ala Met
                 85                  90                  95 ggt gtt gac tat att gat gaa agt gaa gtt ctg acg ccg gct gac gaa     336
Gly Val Asp Tyr Ile Asp Glu Ser Glu Val Leu Thr Pro Ala Asp Glu
            100                 105                 110 gaa ttt cat tta aat aaa aat gaa tac aca gtt cct ttt gtc tgt ggc     384
Glu Phe His Leu Asn Lys Asn Glu Tyr Thr Val Pro Phe Val Cys Gly
        115                 120                 125 tgc cgt gat ctt ggt gaa gca aca cgc cgt att gcg gaa ggt gct tct     432
Cys Arg Asp Leu Gly Glu Ala Thr Arg Arg Ile Ala Glu Gly Ala Ser
    130                 135                 140 atg ctt cgc aca aaa ggt gag cct gga aca ggt aat att gtt gag gct     480
Met Leu Arg Thr Lys Gly Glu Pro Gly Thr Gly Asn Ile Val Glu Ala
145                 150                 155                 160 gtt cgc cat atg cgt aaa gtt aac gct caa gtg cgc aaa gta gtt gcg     528
```

```
                Val Arg His Met Arg Lys Val Asn Ala Gln Val Arg Lys Val Val Ala
                            165                 170                 175 atg agt gag gat gag cta atg aca gaa gcg aaa aac cta ggt gct cct     576
Met Ser Glu Asp Glu Leu Met Thr Glu Ala Lys Asn Leu Gly Ala Pro
                180                 185                 190 tac gag ctt ctt ctt caa att aaa aaa gac ggc aag ctt cct gtc gtt     624
Tyr Glu Leu Leu Leu Gln Ile Lys Lys Asp Gly Lys Leu Pro Val Val
                195                 200                 205 aac ttt gcc gct ggc ggc gta gca act cca gct gat gct gct ctc atg     672
Asn Phe Ala Ala Gly Gly Val Ala Thr Pro Ala Asp Ala Ala Leu Met
            210                 215                 220 atg cag ctt ggt gct gac gga gta ttt gtt ggt tct ggt att ttt aaa     720
Met Gln Leu Gly Ala Asp Gly Val Phe Val Gly Ser Gly Ile Phe Lys
225                 230                 235                 240 tca gac aac cct gct aaa ttt gcg aaa gca att gtg gaa gca aca act     768
Ser Asp Asn Pro Ala Lys Phe Ala Lys Ala Ile Val Glu Ala Thr Thr
                245                 250                 255 cac ttt act gat tac aaa tta atc gct gag ttg tca aaa gag ctt ggt     816
His Phe Thr Asp Tyr Lys Leu Ile Ala Glu Leu Ser Lys Glu Leu Gly
                260                 265                 270 act gca atg aaa ggg att gaa atc tca aac tta ctt cca gaa cag cgt     864
Thr Ala Met Lys Gly Ile Glu Ile Ser Asn Leu Leu Pro Glu Gln Arg
            275                 280                 285 atg caa gaa cgc ggc tgg aga tct att gaa ggc cgc atg aag ttc tcc     912
Met Gln Glu Arg Gly Trp Arg Ser Ile Glu Gly Arg Met Lys Phe Ser
        290                 295                 300 gtc tcc gcc gcc gtc ctc gcc ttc gcc gcc tcc gtc gcc gcc ctc cct     960
Val Ser Ala Ala Val Leu Ala Phe Ala Ala Ser Val Ala Ala Leu Pro
305                 310                 315                 320 cag cac gac tcc gcc gcc ggc aac ggc aac ggc gtc ggc aac aag ttc    1008
Gln His Asp Ser Ala Ala Gly Asn Gly Asn Gly Val Gly Asn Lys Phe
                325                 330                 335 cct gtc cct gac gac gtc acc gtc aag cag gcc acc gac aag tgc ggc    1056
Pro Val Pro Asp Asp Val Thr Val Lys Gln Ala Thr Asp Lys Cys Gly
                340                 345                 350 gac cag gcc cag ctc tcc tgc tgc aac aag gcc acc tac gcc ggc gac    1104
Asp Gln Ala Gln Leu Ser Cys Cys Asn Lys Ala Thr Tyr Ala Gly Asp
            355                 360                 365 gtc ctc acc gac atc gac gag ggc atc ctc gcc ggc ctc ctc aag aac    1152
Val Leu Thr Asp Ile Asp Glu Gly Ile Leu Ala Gly Leu Leu Lys Asn
        370                 375                 380 ctc atc ggc ggc ggc tcc ggc tcc gag ggc ctc ggc ctc ttc gac cag    1200
Leu Ile Gly Gly Gly Ser Gly Ser Glu Gly Leu Gly Leu Phe Asp Gln
385                 390                 395                 400 tgc gtc aag ctc gac ctc cag atc tcc gtc atc ggc atc cct atc cag    1248
Cys Val Lys Leu Asp Leu Gln Ile Ser Val Ile Gly Ile Pro Ile Gln
                405                 410                 415 gac ctc ctc aac cag gtc aac aag cag tgc aag cag aac atc gcc tgc    1296
Asp Leu Leu Asn Gln Val Asn Lys Gln Cys Lys Gln Asn Ile Ala Cys
                420                 425                 430 tgc cag aac tcc cct tcc gac gcc acc ggc tcc ctc gtc aac ctc ggc    1344
Cys Gln Asn Ser Pro Ser Asp Ala Thr Gly Ser Leu Val Asn Leu Gly
            435                 440                 445 ctc ggc aac cct tgc atc cct gtc tcc ctc ctc cat atg gga tct cat    1392
Leu Gly Asn Pro Cys Ile Pro Val Ser Leu Leu His Met Gly Ser His
        450                 455                 460 cac cat cac cat cac                                                 1407
His His His His His
465
```

<210> SEQ ID NO 24
<211> LENGTH: 469
<212> TYPE: PRT
<213> ORGANISM: Artificial Sequence
<220> FEATURE:
<223> OTHER INFORMATION: basf-yaad-Xa-BASF1-his: fusion of Bacillus
subtilis yaaD and N-terminal factor Xa proteinase cleavage site
and artificial hydrophobin BASF1; BASF1 from chemically
synthesized polynucleotide

<400> SEQUENCE: 24

```
Met Ala Gln Thr Gly Thr Glu Arg Val Lys Arg Gly Met Ala Glu Met
1               5                   10                  15

Gln Lys Gly Gly Val Ile Met Asp Val Ile Asn Ala Glu Gln Ala Lys
            20                  25                  30

Ile Ala Glu Ala Gly Ala Val Ala Val Met Ala Leu Glu Arg Val
        35                  40                  45

Pro Ala Asp Ile Arg Ala Ala Gly Gly Val Ala Arg Met Ala Asp Pro
    50                  55                  60

Thr Ile Val Glu Glu Val Met Asn Ala Val Ser Ile Pro Val Met Ala
65                  70                  75                  80

Lys Ala Arg Ile Gly His Ile Val Glu Ala Arg Val Leu Glu Ala Met
                85                  90                  95

Gly Val Asp Tyr Ile Asp Glu Ser Glu Val Leu Thr Pro Ala Asp Glu
            100                 105                 110

Glu Phe His Leu Asn Lys Asn Glu Tyr Thr Val Pro Phe Val Cys Gly
        115                 120                 125

Cys Arg Asp Leu Gly Glu Ala Thr Arg Arg Ile Ala Glu Gly Ala Ser
    130                 135                 140

Met Leu Arg Thr Lys Gly Glu Pro Gly Thr Gly Asn Ile Val Glu Ala
145                 150                 155                 160

Val Arg His Met Arg Lys Val Asn Ala Gln Val Arg Lys Val Val Ala
                165                 170                 175

Met Ser Glu Asp Glu Leu Met Thr Glu Ala Lys Asn Leu Gly Ala Pro
            180                 185                 190

Tyr Glu Leu Leu Leu Gln Ile Lys Lys Asp Gly Lys Leu Pro Val Val
        195                 200                 205

Asn Phe Ala Ala Gly Gly Val Ala Thr Pro Ala Asp Ala Ala Leu Met
    210                 215                 220

Met Gln Leu Gly Ala Asp Gly Val Phe Val Gly Ser Gly Ile Phe Lys
225                 230                 235                 240

Ser Asp Asn Pro Ala Lys Phe Ala Lys Ala Ile Val Glu Ala Thr Thr
                245                 250                 255

His Phe Thr Asp Tyr Lys Leu Ile Ala Glu Leu Ser Lys Glu Leu Gly
            260                 265                 270

Thr Ala Met Lys Gly Ile Glu Ile Ser Asn Leu Leu Pro Glu Gln Arg
        275                 280                 285

Met Gln Glu Arg Gly Trp Arg Ser Ile Glu Gly Arg Met Lys Phe Ser
    290                 295                 300

Val Ser Ala Ala Val Leu Ala Phe Ala Ala Ser Val Ala Ala Leu Pro
305                 310                 315                 320

Gln His Asp Ser Ala Ala Gly Asn Gly Asn Gly Val Gly Asn Lys Phe
                325                 330                 335

Pro Val Pro Asp Asp Val Thr Val Lys Gln Ala Thr Asp Lys Cys Gly
            340                 345                 350
```

```
Asp Gln Ala Gln Leu Ser Cys Cys Asn Lys Ala Thr Tyr Ala Gly Asp
        355                 360                 365
Val Leu Thr Asp Ile Asp Glu Gly Ile Leu Ala Gly Leu Leu Lys Asn
    370                 375                 380
Leu Ile Gly Gly Gly Ser Gly Ser Glu Gly Leu Gly Leu Phe Asp Gln
385                 390                 395                 400
Cys Val Lys Leu Asp Leu Gln Ile Ser Val Ile Gly Ile Pro Ile Gln
                405                 410                 415
Asp Leu Leu Asn Gln Val Asn Lys Gln Cys Lys Gln Asn Ile Ala Cys
            420                 425                 430
Cys Gln Asn Ser Pro Ser Asp Ala Thr Gly Ser Leu Val Asn Leu Gly
        435                 440                 445
Leu Gly Asn Pro Cys Ile Pro Val Ser Leu Leu His Met Gly Ser His
    450                 455                 460
His His His His His
465

<210> SEQ ID NO 25
<211> LENGTH: 28
<212> TYPE: DNA
<213> ORGANISM: Artificial Sequence
<220> FEATURE:
<223> OTHER INFORMATION: Chemically synthesized Hal570 primer

<400> SEQUENCE: 25
gcgcgcccat ggctcaaaca ggtactga                                    28

<210> SEQ ID NO 26
<211> LENGTH: 28
<212> TYPE: DNA
<213> ORGANISM: Artificial Sequence
<220> FEATURE:
<223> OTHER INFORMATION: Chemically synthesized Hal571 primer

<400> SEQUENCE: 26
gcagatctcc agccgcgttc ttgcatac                                    28

<210> SEQ ID NO 27
<211> LENGTH: 30
<212> TYPE: DNA
<213> ORGANISM: Artificial Sequence
<220> FEATURE:
<223> OTHER INFORMATION: Chemically synthesized Hal572 primer

<400> SEQUENCE: 27
ggccatggga ttaacaatag gtgtactagg                                  30

<210> SEQ ID NO 28
<211> LENGTH: 33
<212> TYPE: DNA
<213> ORGANISM: Artificial Sequence
<220> FEATURE:
<223> OTHER INFORMATION: Chemically synthesized Hal573 primer

<400> SEQUENCE: 28
gcagatctta caagtgcctt ttgcttatat tcc                              33

<210> SEQ ID NO 29
<211> LENGTH: 38
<212> TYPE: DNA
<213> ORGANISM: Artificial Sequence
<220> FEATURE:
<223> OTHER INFORMATION: Chemically synthesized KaM416 primer
```

<400> SEQUENCE: 29
gcagcccatc agggatccct cagccttggt accagcgc                                    38

<210> SEQ ID NO 30
<211> LENGTH: 50
<212> TYPE: DNA
<213> ORGANISM: Artificial Sequence
<220> FEATURE:
<223> OTHER INFORMATION: Chemically synthesized KaM417 primer

<400> SEQUENCE: 30
cccgtagcta gtggatccat tgaaggccgc atgaagttct ccgtctccgc                       50

<210> SEQ ID NO 31
<211> LENGTH: 45
<212> TYPE: DNA
<213> ORGANISM: Artificial Sequence
<220> FEATURE:
<223> OTHER INFORMATION: Chemically synthesized KaM434 primer

<400> SEQUENCE: 31
gctaagcgga tccattgaag gccgcatgaa gttctccatt gctgc                            45

<210> SEQ ID NO 32
<211> LENGTH: 30
<212> TYPE: DNA
<213> ORGANISM: Artificial Sequence
<220> FEATURE:
<223> OTHER INFORMATION: Chemically synthesized KaM435 primer

<400> SEQUENCE: 32
ccaatgggga tccgaggatg gagccaaggg                                             30

<210> SEQ ID NO 33
<211> LENGTH: 38
<212> TYPE: DNA
<213> ORGANISM: Artificial Sequence
<220> FEATURE:
<223> OTHER INFORMATION: Chemically synthesized KaM418 primer

<400> SEQUENCE: 33
ctgccattca ggggatccca tatggaggag ggagacag                                    38

<210> SEQ ID NO 34
<211> LENGTH: 32
<212> TYPE: DNA
<213> ORGANISM: Artificial Sequence
<220> FEATURE:
<223> OTHER INFORMATION: Chemically synthesized KaM464 primer

<400> SEQUENCE: 34
cgttaaggat ccgaggatgt tgatgggggt gc                                          32

<210> SEQ ID NO 35
<211> LENGTH: 35
<212> TYPE: DNA
<213> ORGANISM: Artificial Sequence
<220> FEATURE:
<223> OTHER INFORMATION: Chemically synthesized KaM465 primer

<400> SEQUENCE: 35
gctaacagat ctatgttcgc ccgtctcccc gtcgt                                       35

DRILLING MUD CONTAINING HYDROPHOBIN

RELATED APPLICATIONS

This application is a national stage application under 35 U.S.C. §371 of PCT/EP2006/061134, filed Mar. 29, 2006, which claims benefit of European application 05007208.1, filed Apr. 1, 2005, and European application 05016962.2, filed Aug. 4, 2005.

SEQUENCE LISTING SUBMISSION

The Sequence Listing associated with this application is filed in electronic format via BPS-Web and hereby incorporated by reference into the specification in its entirety. The name of the text file containing the Sequence Listing is Revised_Sequence_List__13156__00117_US. The size of the text file is 70.7 KB, and the text file was created on Jan. 5, 2009.

DESCRIPTION

The present invention relates to a drilling mud comprising a hydrophobin or one of its derivatives and to the use of a hydrophobin as an assistant for a drilling mud.

Drilling muds generally have the task of simplifying the often difficult drilling operation in the development of new deposits for, for example, mineral oil or natural gas. The intention is to support both the drilling operation and the conveying of the rock splinters generated in the process. The drill bit and the drilling column have to be lubricated and cooled. Moreover, the hydrostatic pressure of the deposit has to be compensated for, which is why drilling muds with an elevated specific weight are frequently used. The walls of the bore should also be lined.

Important properties of a commercially utilizable drilling mud include suitable viscosity and flow properties, density, thermal stability, emulsifying and dispersion capacity, pH control and, not least, also a high degree of environmental compatibility.

Since the search for new raw materials is being continued in many parts of the world, and deep drilling frequently also has to be undertaken at isolated locations, for example far from the coast or in the middle of the jungle, there is a need for new drilling assistants, especially assistants for a drilling mud which satisfies the high technical requirements and can be produced inexpensively and used on site. In addition, a drilling mud should also be storage-stable and be usable over a prolonged period.

It is also of particular significance that a drilling mud does not lead to lasting damage in the animal and plant world in the event of release into the environment.

Hydrophobins are small proteins of from about 100 to 150 amino acids, which can be produced from filamentous fungi, for example from *Schizophyllum* commune. They generally have 8 cysteine units per molecule.

Hydrophobins have a marked affinity for interfaces and are therefore suitable for coating surfaces, for example in order to alter the properties of the interfaces by forming amphiphatic membranes. For example, the plastic Teflon can be coated by means of hydrophobins to obtain a hydrophilic surface.

Hydrophobins can be isolated from natural sources. Moreover, synthetic production processes for hydrophobins and their derivatives are known. For example, German patent application DE 10 2005 007 480.4 discloses a production process for hydrophobins and derivatives thereof.

The prior art has already proposed the use of hydrophobins for various applications.

For instance, EP-A 05 016 962 describes the use of proteins to improve phase separation of, for example, oil/water or fuel/water mixtures. It is known to those skilled in the art that particular amphiphilic molecules, depending on the use concentration and surrounding medium, can have either stabilizing or destabilizing effects on phase interfaces.

WO 96/41882 proposes the use of hydrophobins as emulsifiers, thickeners, surface-active substances, for hydrophilizing hydrophobic surfaces, for improving the water resistance of hydrophilic substrates, for producing oil-in-water emulsions or water-in-oil emulsions. Also proposed are pharmaceutical applications, such as the production of ointments or creams, and cosmetic applications, such as skin protection or the production of shampoos or hair rinses. WO 96/41882 additionally describes compositions, for example for pharmaceutical applications, comprising a hydrophobin.

EP-A 1 252 516 discloses the coating of windows, contact lenses, biosensors, medical devices, vessels for performing tests or for storage, ships' hulls, solid particles or frames or chassis of passenger vehicles with a hydrophobin-comprising solution at a temperature of from 30 to 80° C.

WO 03/53383 describes the use of hydrophobin for treating keratin materials in cosmetic applications.

WO 03/10331 discloses that hydrophobins have surface-active properties. For instance, a hydrophobin-coated sensor is disclosed, for example a test electrode to which further substances, for example electroactive substances, antibodies or enzymes, are bonded non-covalently.

WO 2004/000880 presents the coating of surfaces with hydrophobin or hydrophobin-like substances. It is also disclosed that oil-in-water or water-in-oil emulsions too can be stabilized by adding hydrophobins.

WO 01/74864, which relates to hydrophobin-like proteins, also states that they can be used to stabilize dispersions and emulsions.

The use of, proteins for phase separation is also known in principle. For instance, GB 195,876 describes a process for breaking water-in-oil emulsions using colloids. The colloids mentioned are, by way of example, proteins such as gelatins, casein, albumin or polysaccharides such as gum arabic or gum tragacanth.

JP-A 11-169177 discloses the use of proteins with lipase activity for breaking emulsions.

WO 01/60916 discloses the use of surfactant-free mixtures of at least one water-soluble protein, at least one water-soluble polysaccharide and at least one water-soluble polymer, for example polyethylene oxide, for various uses, also including for the emulsification of crude oil.

However, none of the documents cited discloses the use of hydrophobins as assistants in drilling muds.

The present invention provides the use of a hydrophobin as an assistant for a drilling mud, the hydrophobin being used especially as an emulsifier in a drilling mud.

The hydrophobin used is preferably a fusion hydrophobin, especially a fusion hydrophobin selected from the group mentioned later of yaad-Xa-dewA-his (SEQ ID NO: 20), yaad-Xa-rodA-his (SEQ ID NO: 22) or yaad-Xa-basf1-his (SEQ ID NO: 24), where yaad may also be a truncated fusion partner yaad' having from 20 to 293 amino acids.

Drilling muds consist generally of one or more liquids, for example water, crude oil and organic additives or solvents, and of suspended or dissolved solids. Depending on the type of main liquid component, a distinction is drawn between aqueous drilling muds, oil-based drilling muds and synthetic drilling muds.

In the inventive drilling mud, preference is given to using an oil-based drilling mud (e.g. diesel oil, mineral oil). Preference is likewise given to using the hydrophobin (it is also possible to use a plurality of hydrophobins simultaneously) in an amount of from 0.1 to 10 000 ppm, preferably from 1 to 1000 ppm, especially from 1 to 600 ppm, based in each case on the overall composition. It is one of the advantages that the amount of hydrophobin used is significantly less than in the case of conventional emulsifiers, which are used in the range from 2 to 10% by weight.

The drilling mud is preferably an oil-based drilling mud which comprises from 40 to 95% by weight, preferably from 70 to 95% by weight, of at least one oil component, from 2 to 80% by weight, preferably from 2 to 30% by weight, of water, and if appropriate further components.

Useful further components include, for example, the following substances:

a) salts (for example alkali metal and alkaline earth metal chlorides, alkali metal and alkaline earth metal bromides, alkali metal and alkaline earth metal carbonates; these salts often also serve to control the pH),
b) additives for compensating for liquid losses (for example bentonites, starch, cellulose or derivatives thereof),
c) wetting agents [in order to make the abovementioned additives (for example bentonites) oil-wettable],
d) flow improvers (which reduce the flow resistance, for example acrylic resins, polysiloxanes, polyurethanes),
e) additives for increasing the specific weight of the drilling mud (for example baryte, hematite, magnetite, ilmenite, siderite, dolomite, calcite, sodium chloride),
f) emulsifiers (for example salts of fatty acids; polyamides),
g) other additives, for example dispersants, fluid loss additives, polymers or copolymers, amines (for example polyacrylamides),
h) viscosity-increasing additives (for example bentonite, attapulgite).

In a preferred embodiment of the invention, at least one further compound which improves the emulsion formation is used as well as the hydrophobin.

The invention also relates to a process for drilling a borehole, especially for developing underground deposits, especially of oil and gas, in which a drilling mud which comprises at least one hydrophobin or a derivative thereof is used. Preference is given to using the abovementioned fusion hydrophobins.

In the drilling process, an oil-based drilling mud is usually, used, which comprises from 40 to 95% by weight of at least one oil component, for example biodiesel, from 2 to 60% by weight of water (for example fresh water or seawater) and if appropriate further components.

The present invention further provides a drilling mud itself, comprising at least one hydrophobin.

In a particular embodiment, the drilling mud comprises from 70 to 95% by weight of at least one oil component (for example biodiesel), from 2 to 30% by weight of water, and if appropriate up to 13% by weight of further components (for example bentonite and/or calcium chloride).

The invention also relates to a process for producing a drilling mud, in which the hydrophobin component and the remaining components of the drilling mud are mixed intimately. This can be done at an industrial production site or else on site, for example on a drilling platform.

The use of proteins such as hydrophobin as drilling assistants has the advantage that they are naturally occurring or nature-analogous substances which are biodegradable and thus do not lead to lasting damage to the environment.

In many applications on a large scale, for example when drilling for oil deposits, a crucial factor is very long-lasting usability of the assistants used. It was an object of the invention to provide an improved process for undertaking earth drilling using specific proteins.

In the context of the present invention, a hydrophobin is also understood to mean derivatives thereof or modified hydrophobin. Modified or derivatized hydrophobins may, for example, be hydrophobin fusion proteins or proteins which have an amino acid sequence which has at least 60%, for example at least 70%, in particular at least 80%, more preferably at least 90%, especially preferably at least 95% identity with the sequence of a hydrophobin, and which also satisfy the biological properties of a hydrophobin to an extent of 50%, for example to an extent of 60%, in particular to an extent of 70%, more preferably to an extent of 80%, especially the property that the surface properties are altered by coating with these proteins such that the contact angle of a water droplet before and after the coating of a glass surface with the protein is increased by at least 20°, preferably by at least 25°, in particular by at least 30°.

It has been found that, surprisingly, hydrophobins or derivatives thereof improve the drilling performance in the exploration and development of deposits. This is also based on the fact that rapid phase separation of the drilling mud and of the material conveyed is prevented. In this context, even small amounts of hydrophobin are extremely effective.

For the definition of hydrophobins, what is crucial is the structural specificity and not the sequence specificity of the hydrophobins. The amino acid sequence of the natural hydrophobins is very diverse, but they all have a highly characteristic pattern of 8 conserved cysteine residues. These residues form four intramolecular disulfide bridges. The N terminus and C terminus are variable over a relatively wide range. It is possible here to add on fusion partner proteins having a length of from 10 to 500 amino acids by means of molecular biology techniques known to those skilled in the art. Moreover, hydrophobins and derivatives thereof are understood in the context of the present invention to mean proteins with a similar structure and functional equivalence.

In the context of the present invention, the term "hydrophobins" should be understood hereinafter to mean polypeptides of the general structural formula (I)

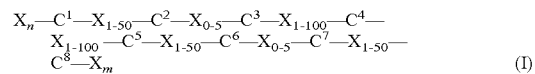

$$X_n\text{—}C^1\text{—}X_{1\text{-}50}\text{—}C^2\text{—}X_{0\text{-}5}\text{—}C^3\text{—}X_{1\text{-}100}\text{—}C^4\text{—}$$
$$X_{1\text{-}100}\text{—}C^5\text{—}X_{1\text{-}50}\text{—}C^6\text{—}X_{0\text{-}5}\text{—}C^7\text{—}X_{1\text{-}50}\text{—}$$
$$C^8\text{—}X_m \quad (I)$$

where X may be any of the 20 naturally occurring amino acids (Phe, Leu, Ser, Tyr, Cys, Trp, Pro, His, Gln, Arg, Ile Met, Thr, Asn, Lys, Val, Ala, Asp, Glu, Gly). In the formula, X may be the same or different in each case. The indices beside X are each the number of amino acids, C is cysteine, alanine, serine, glycine, methionine or threonine, where at least four of the residues designated with C are cysteine, and the indices n and m are each independently natural numbers between 0 and 500, preferably between 15 and 300.

The polypeptides of the formula (I) are also characterized by the property that, at room temperature, after coating a glass surface, they bring about an increase in the contact angle of a water droplet of at least 200, preferably at least 250 and more preferably 300, compared in each case with the contact angle of an equally large water droplet with the uncoated glass surface.

The amino acids designated with $C^1$ to $C^8$ are preferably cysteines; however, they may also be replaced by other amino acids with similar space-filling, preferably by alanine, serine, threonine, methionine or glycine. However, at least four, preferably at least 5, more preferably at least 6 and in particular at least 7 of positions $C^1$ to $C^8$ should consist of cysteines. In the inventive proteins, cysteines may either be present in reduced form or form disulfide bridges with one another. Particular preference is given to the intramolecular formation of C—C bridges, especially that with at least one intramolecular disulfide bridge, preferably 2, more preferably 3 and most preferably 4 intramolecular disulfide bridges. In the case of the above-described exchange of cysteines for amino acids with similar space-filling, such C positions are advantageously exchanged in pairs which can form intramolecular disulfide bridges with one another.

If cysteines, serines, alanines, glycines, methionines or threonines are also used in the positions designated with X, the numbering of the individual C positions in the general formulae can change correspondingly.

Preference is given to using hydrophobins of the general formula (II)

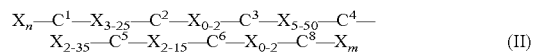

to perform the present invention, where X, C and the indices beside X and C are each as defined above, the indices n and m are each numbers between 0 and 300, and the proteins additionally feature the above-illustrated change in contact angle, and, furthermore, at least 6 of the residues designated with C are cysteine. More preferably, all C residues are cysteine.

Particular preference is given to using hydrophobins of the general formula (III)

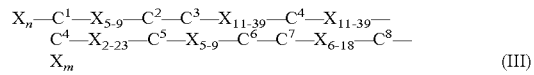

where X, C and the indices besides X are each as defined above, the indices n and m are each numbers between 0 and 200, and the proteins additionally feature the above-illustrated change in contact angle, and at least 6 of the residues designated with C are cysteine. More preferably, all C residues are cysteine.

The $X_n$ and $X_m$ residues may be peptide sequences which naturally are also joined to a hydrophobin. However, one or both residues may also be peptide sequences which are naturally not joined to a hydrophobin. This is also understood to mean those $X_n$ and/or $X_m$ residues in which a peptide sequence which occurs naturally in a hydrophobin is lengthened by a peptide sequence which does not occur naturally in a hydrophobin.

If $X_n$ and/or $X_m$ are peptide sequences which are not naturally bonded into hydrophobins, such sequences are generally at least 20, preferably at least 35, more preferably at least 50 and most preferably at least 100 amino acids in length. Such a residue which is not joined naturally to a hydrophobin will also be referred to hereinafter as a fusion partner. This is intended to express that the proteins may consist of at least one hydrophobin moiety and a fusion partner moiety which do not occur together in this form in nature.

The fusion partner moiety may be selected from a multitude of proteins. It is also possible for a plurality of fusion partners to be joined to one hydrophobin moiety, for example on the amino terminus ($X_n$) and on the carboxyl terminus ($X_m$) of the hydrophobin moiety. However, it is also possible, for example, for two fusion partners to be joined to one position ($X_n$ or $X_m$) of the inventive protein.

Particularly suitable fusion partners are proteins which naturally occur in microorganisms, especially in *E. coli* or *Bacillus subtilis*. Examples of such fusion partners are the sequences yaad (SEQ ID NO: 15 and 16), yaae (SEQ ID NO: 17 and 18), and thioredoxin.

Also very suitable are fragments or derivatives of these sequences which comprise only some, for example from 70 to 99%, preferentially from 5 to 50% and more preferably from 10 to 40% of the sequences mentioned, or in which individual amino acids or nucleotides have been changed compared to the sequence mentioned, in which case the percentages are each based on the number of amino acids.

In a further preferred embodiment, the fusion hydrophobin, as well as the fusion partner as an $X_n$ or $X_m$ group, also has a so-called affinity domain (affinity tag/affinity tail). In a manner known in principle, this comprises anchor groups which can interact with particular complementary groups and can serve for easier workup and purification of the proteins. Examples of such affinity domains comprise $(His)_k$, $(Arg)_k$, $(Asp)_k$, $(Phe)_k$ or $(Cys)_k$ groups, where k is generally a natural number from 1 to 10. It may preferably be a $(His)_k$ group, where k is from 4 to 6.

The proteins used in accordance with the invention as hydrophobins or derivatives thereof may also be modified in their polypeptide sequence, for example by glycosylation, acetylation or else by chemical crosslinking, for example with glutaraldehyde.

One property of the hydrophobins or derivatives thereof used in accordance with the invention is the change in surface properties when the surfaces are coated with the proteins. The change in the surface properties can be determined experimentally, for example, by measuring the contact angle of a water droplet before and after the coating of the surface with the protein and determining the difference of the two measurements.

The performance of contact angle measurements is known in principle to those skilled in the art. The measurements are based on room temperature and water droplets of 5 µl and the use of glass plates as substrates. The exact experimental conditions for an example of a suitable method for measuring the contact angle are given in the experimental section. Under the conditions mentioned there, the fusion proteins used in accordance with the invention have the property of increasing the contact angle by at least 20°, preferably at least 25°, more preferably at least 30°, compared in each case with the contact angle of an equally large water droplet with the uncoated glass surface.

Particularly preferred hydrophobins for performing the present invention are the hydrophobins of the dewA, rodA, hypA, hypB, sc3, basf1, basf2 type, which are characterized structurally in the sequence listing which follows. They may also only be parts or derivatives thereof. It is also possible for a plurality of hydrophobin moieties, preferably 2 or 3, of identical or different structure to be bonded to one another and to be bonded to a corresponding suitable polypeptide sequence which is not bonded to a hydrophobin in nature.

Also particularly suitable in accordance with the invention are the fusion proteins yaad-Xa-dewA-his (SEQ ID NO: 20), yaad-Xa-rodA-his (SEQ ID NO: 22) or yaad-Xa-basf1-his (SEQ ID NO: 24), with the polypeptide sequences specified in brackets and the nucleic acid sequences which code therefor, especially the sequences according to SEQ ID NO: 19, 21, 23. Proteins which, proceeding from the polypeptide sequences shown in SEQ ID NO. 20, 22 or 24, arise through exchange, insertion or deletion of from at least one up to 10, preferably 5 amino acids, more preferably 5% of all amino acids, and which still have the biological property of the starting proteins to an extent of at least 50%, are also particularly preferred embodiments. A biological property of the proteins is understood here to mean the change in the contact angle by at least 200, which has already been described.

Derivatives particularly suitable for performing the invention are residues derived from yaad-Xa-dewA-his (SEQ ID NO: 20), yaad-Xa-rodA-his (SEQ ID NO: 22) or yaad-Xa-basf1-his (SEQ ID NO: 24) by truncating the yaad fusion partner. Instead of the complete yaad fusion partner (SEQ ID NO: 16) with 294 amino acids, it may be advantageous to use a truncated yaad residue. The truncated residue should, though, comprise at least 20, more preferably at least 35 amino acids. For example, a truncated radical having from 20 to 293, preferably from 25 to 250, more preferably from 35 to 150 and, for example, from 35 to 100 amino acids may be used.

A cleavage site between the hydrophobin and the fusion partner or the fusion partners can be utilized to release the pure hydrophobin in underivatized form (for example by BrCN cleavage at methionin, factor Xa cleavage, enterokinase cleavage, thrombin cleavage, TEV cleavage, etc.).

It is also possible to generate fusion proteins in succession from one fusion partner, for example yaad or yaae, and a plurality of hydrophobins, even of different sequence, for example DewA-RodA or Sc3-DewA, Sc3-RodA. It is equally possible to use hydrophobin; fragments (for example N- or C-terminal truncations) or mutein which have up to 70% homology. The optimal constructs are in each case selected in relation to the particular use, i.e. the liquid phase to be separated.

The hydrophobins used in accordance with the invention or present in the inventive compositions can be prepared chemically by known methods of peptide synthesis, for example by Merrifield solid-phase synthesis.

Naturally occurring hydrophobins can be isolated from natural sources by means of suitable methods. Reference is made by way of example to Wösten et. al., Eur. J. Cell Bio. 63, 122-129 (1994) or WO 96/41882.

Fusion proteins can be prepared preferably by genetic engineering methods, in which one nucleic acid sequence, especially DNA sequence, encoding the fusion partner and one encoding the hydrophobin moiety are combined in such a way that the desired protein is generated in a host organism as a result of gene expression of the combined nucleic acid sequence. Such a preparation process is disclosed, for example, in DE 102005007480.4.

Suitable host organisms (production organisms) for the preparation method mentioned may be prokaryotes (including the Archaea) or eukaryotes, particularly bacteria including halobacteria and methanococcia, fungi, insect cells, plant cells and mammalian cells, more preferably *Escherichia coli, Bacillus subtilis, Bacillus megaterium, Aspergillus oryzae, Aspergillus nidulans, Aspergillus niger, Pichia pastoris, Pseudomonas* spec., *lactobacilli, Hansenula polymorpha, Trichoderma reesei*, SF9 (or related cells), among others.

The invention is also based on the use of expression constructs comprising, under the genetic control of regulatory nucleic acid sequences, a nucleic acid sequence which encodes a polypeptide used in accordance with the invention, and also vectors comprising at least one of these expression constructs. Constructs used preferably comprise, 5' upstream from the particular encoding sequence, a promoter and, 3' downstream, a terminator sequence and if appropriate further customary regulatory elements, in each case linked operatively to the encoding sequence. In the context of the present invention, an "operative linkage" is understood to mean the sequential arrangement of promoter, encoding sequence, terminator and if appropriate further regulatory elements such that each of the regulatory elements can fulfil its function as intended in the expression of the encoding sequence.

Examples of operatively linkable sequences are targeting sequences, and also enhancers, polyadenylation signals and the like.

Further regulatory elements comprise selectable markers, amplification signals, replication origins and the like. Suitable regulatory sequences are, for example, described in Goeddel, Gene Expression Technology: Methods in Enzymology 185, Academic Press, San Diego, Calif. (1990).

In addition to these regulation sequences, the natural regulation of these sequences may still be present upstream of the actual structural genes and, if appropriate, have been genetically modified so as to switch off the natural regulation and increase the expression of the genes.

A preferred nucleic acid construct also advantageously comprises one or more so-called "enhancer" sequences, joined functionally to the promoter, which enable increased expression of the nucleic acid sequence. Also at the 3' end of the DNA sequences, it is possible for additional advantageous sequences to be inserted, such as further regulatory elements or terminators.

The nucleic acids may be present in the construct in one or more copies. It is also possible for further markers such as antibiotic resistances or genes which complement auxotrophies to be present in the construct, if appropriate for selection for the construct.

Advantageous regulation sequences for the preparation are present, for example, in promoters such as the cos, tac, trp, tet, trp-tet, Ipp, lac, Ipp-lac, lacIq-T7, T5, T3, gal, trc, ara, rhaP (rhaPBAD) SP6, lambda-PR or imlambda-P promoter, which advantageously find use in Gram-negative bacteria. Further advantageous regulation sequences are present, for example, in the Gram-positive promoters amy and SP02, and in the yeast or fungal promoters ADC1, MFalpha, AC, P-60, CYC1, GAPDH, TEF, rp28, ADH.

It is also possible to use synthetic promoters for the regulation.

For expression in a host organism, the nucleic acid construct is advantageously inserted into a vector, for example a plasmid or a phage which enables optimal expression of the genes in the host. Apart from plasmids and phages, vectors are also understood to mean all other vectors known to those skilled in the art, for example viruses such as SV40, CMV, baculovirus and adenovirus, transposons, IS elements, phasmids, cosmids, and linear or circular DNA, and also the *Agrobacterium* system.

These vectors can be replicated autonomously in the host organism or replicated chromosomally. Suitable plasmids are, for example, in *E. coli* pLG338, pACYC184, pBR322, pUC18, pUC19, pKC30, pRep4, pHS1, pKK223-3, pDHE19.2, pHS2, pPLc236, pMBL24, pLG200, pUR290, pIN-III"3-B1, tgtl1 or pBdCl, in *Streptomyces* plJ101, plJ364, plJ702 or plJ361, in *Bacillus* pUB110, pC194 or pBD214, in *Corynebacterium* pSA77 or pAJ667, in fungi pALS1, pIL2 or pBB116, in yeasts 2alpha, pAG-1, YEp6, YEp13 or pEMBLYe23 or in plants pLGV23, pGHlac+, pBIN19, pAK2004 or pDH51. The plasmids mentioned constitute a small selection of the possible plasmids. Further plasmids are known to those skilled in the art and can be taken, for example, from the book Cloning Vectors (Eds. Pouwels P. H. et al. Elsevier, Amsterdam-New York-Oxford, 1985, ISBN 0 444 904018).

Advantageously, the nucleic acid construct, for the expression of the further genes present, additionally also comprises 3'- and/or 5'-terminal regulatory sequences for enhancing the expression, which are selected for optimal expression depending upon the host organism and gene or genes selected.

These regulatory sequences are intended to enable the controlled expression of the genes and, of the protein expression. Depending on the host organism, this can mean, for example, that the gene is expressed or overexpressed only after induction, or that it is expressed and/or overexpressed immediately.

The regulatory sequences or factors can preferably positively influence and thus increase the gene expression of the genes introduced. Thus, an amplification of the regulatory elements can advantageously be effected at the transcription level by using strong transcription signals such as promoters and/or enhancers. In addition, it is also possible to enhance the translation by, for example, improving the stability of the mRNA.

In a further embodiment of the vector, the vector comprising the nucleic acid construct or the nucleic acid can also be introduced into the microorganisms advantageously in the form of a linear DNA and be integrated into the genome of the host organism by means of heterologous or homologous recombination. This linear DNA can consist of a linearized vector such as a plasmid or only of the nucleic acid construct or the nucleic acid.

For an optimal expression of heterologous genes in organisms, it is advantageous to alter the nucleic acid sequences in accordance with the specific "codon usage" used in the organism. The "codon usage" can be determined easily with reference to computer evaluations of other, known genes of the organism in question.

An expression cassette is prepared by fusion of a suitable promoter with a suitable coding nucleotide sequence and a terminator signal or polyadenylation signal. To this end, common recombination and cloning techniques are used, as described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector which enables an optimal expression of the genes in the host. Vectors are well known to those skilled in the art and can be taken, for example, from "Cloning Vectors" (Pouwels P. H. et al., eds., Elsevier, Amsterdam-New York-Oxford, 1985).

With the aid of vectors, it is possible to prepare recombinant microorganisms which have been transformed, for example, with at least one vector and can be used for the production of the hydrophobins or derivatives thereof used in accordance with the invention. Advantageously, the above-described recombinant constructs are introduced into a suitable host system and expressed. Preference is given to using the cloning and transfection methods familiar to those skilled in the art, for example coprecipitation, protoplast fusion, electroporation, retroviral transfection and the like, in order to bring about the expression of the nucleic acids mentioned in the particular expression system. Suitable systems are described, for example, in Current Protocols in Molecular Biology, F. Ausubel et al., ed., Wiley Interscience, New York 1997, or Sambrook et al. Molecular Cloning: A Laboratory Manual, 2nd edition, Cold Spring Harbor Laboratory, Cold Spring Harbor Laboratory Press, Cold Spring Harbor, N.Y., 1989.

It is also possible to prepare homologously recombined microorganisms. To this end, a vector is prepared which comprises at least a section of a gene to be used or a coding sequence, in which, if appropriate, at least one amino acid deletion, addition or substitution has been introduced in order to change, for example to functionally disrupt, the sequence ("knockout" vector). The sequence introduced may, for example, also be a homolog from a related microorganism or be derived from a mammalian, yeast or insect source. The vector used for the homologous recombination may alternatively be configured such that the endogenous gene in the case of homologous recombination has been mutated or altered in another way, but still encodes the functional protein (for example, the upstream regulatory region can be changed such that the expression of the endogenous protein is changed). The changed section of the gene used in accordance with the invention is in the homologous recombination vector. The construction of suitable vectors for homologous recombination is described, for example, in Thomas, K. R. and Capecchi, M. R. (1987) Cell 51: 503.

In principle, all prokaryotic or eukaryotic organisms are useful as recombinant host organisms for such nucleic acids or such nucleic acid constructs. Advantageously, the host organisms used are microorganisms such as bacteria, fungi or yeasts. Advantageously, Gram-positive or Gram-negative bacteria are used, preferably bacteria from the families Enterobacteriaceae, Pseudomonadaceae, Rhizobiaceae, Streptomydetaceae or Nocardiaceae, more preferably bacteria of the genera *Escherichia, Pseudomonas, Streptomyces, Nocardia, Burkholderia, Salmonella, Agrobacterium* or *Rhodococcus*.

The organisms used in the above-described preparation processes for fusion proteins are, depending on the host organism, grown or cultured in a manner known to those skilled in the art. Microorganisms are generally grown in a liquid medium which comprises a carbon source, usually in the form of sugars, a nitrogen source, usually in the form of organic nitrogen sources such as yeast extract or salts such as ammonium sulfate, trace elements such as iron, manganese and magnesium salts, and also, if appropriate, vitamins, at temperatures between 0 and 100° C., preferably between 10 to 60° C., with oxygen sparging. The pH of the nutrient liquid can be kept at a fixed value, i.e. is regulated or not during the growth. The growth can be effected batchwise, semibatchwise or continuously. Nutrients can be introduced at the start of the fermentation or be replenished semicontinuously or continuously. The enzymes can be isolated from the organisms by the process described in the examples or be used for the reaction as a crude extract.

The hydrophobins used in accordance with the invention, or functional, biologically active fragments thereof, can be prepared by means of a process for recombinant preparation, in which a polypeptide-producing microorganism is cultivated, the expression of the proteins is induced if appropriate and they are isolated from the culture. The proteins can also be produced in this way on an industrial scale if this is desired. The recombinant microorganism can be cultivated and fermented by known processes. Bacteria can be propagated, for example, in TB or LB medium and at a temperature of from 20 to 40° C. and a pH of from 6 to 9. Suitable cultivation conditions are described specifically, for example, in T. Maniatis, E. F. Fritsch and J. Sambrook, Molecular Cloning: A Laboratory Manual, Cold Spring Harbor Laboratory, Cold Spring Harbor, N.Y. (1989).

If the proteins are not secreted into the culture medium, the cells are then disrupted and the product is obtained from the lysate by known protein isolation processes. As desired, the cells can be disrupted by high-frequency ultrasound, by high pressure, for example in a French pressure cell, by osmolysis, by the action of detergents, lytic enzymes or organic solvents, by homogenizers or by combination of a plurality of the processes listed.

The proteins can be purified by known chromatographic processes, such as molecular sieve chromatography (gel filtration) such as Q Sepharose chromatography, ion exchange chromatography and hydrophobic chromatography, and also with other customary processes such as ultrafiltration, crystallization, salting-out, dialysis and native gel electrophoresis. Suitable processes are described, for example, in Cooper, F. G., Biochemische Arbeitsmethoden [Biochemical Techniques], Verlag Walter de Gruyter, Berlin, New York, or in Scopes, R., Protein Purification, Springer Verlag, New York, Heidelberg, Berlin.

It may be particularly advantageous to ease the isolation and purification of the fusion hydrophobins by providing them with specific anchor groups which can bind to corresponding complementary groups on solid supports, especially suitable polymers. Such solid supports may, for example, be used as a filling for chromatography columns, and the efficiency of the separation can generally be increased significantly in this manner. Such separation processes are also known as affinity chromatography. For the incorporation of the anchor groups, it is possible to use, in the preparation of the proteins, vector systems or oligonucleotides which extend the cDNA by particular nucleotide sequences and hence encode altered proteins or fusion proteins. For easier purification, modified proteins comprise so-called "tags" which function as anchors, for example the modification known as the hexa-histidine anchor. Fusion hydrophobins modified with histidine anchors can be purified chromatographically, for example, using nickel-Sepharose as the column filling. The fusion hydrophobin can subsequently be eluted again from the column by means of suitable agents for elution, for example an imidazole solution.

In a simplified purification process, it is possible to dispense with the chromatographic purification. To this end, the cells are first removed from the fermentation broth by means of a suitable method, for example by microfiltration or by centrifugation. Subsequently, the cells can be disrupted by means of suitable methods, for example by means of the methods already mentioned above, and the cell debris can be separated from the inclusion bodies. The latter can advantageously be effected by centrifugation. Finally, the inclusion bodies can be disrupted in a manner known in principle in order to release the fusion hydrophobins. This can be done, for example, by means of acids, bases, and/or detergents. The inclusion bodies with the fusion hydrophobins used in accordance with the invention can generally be dissolved completely even using 0.1 M NaOH within approx. 1 h. The purity of the fusion hydrophobins obtained by this simplified process is generally from 60 to 80% by weight based on the amount of all proteins. The solutions obtained by the simplified purification process described can be used to perform this invention without further purification.

The hydrophobins prepared as described may be used either directly as fusion proteins or, after detachment and removal of the fusion partner, as "pure" hydrophobins.

When a removal of the fusion partner is intended, it is advisable to incorporate a potential cleavage site (specific recognition site for proteases) into the fusion protein between hydrophobin moiety and fusion partner moiety. Suitable cleavage sites are especially those peptide sequences which otherwise occur neither in the hydrophobin moiety nor in the fusion partner moiety, which can be determined easily with bioinformatic tools. Particularly suitable examples are BrCN cleavage at methionine, or protease-mediated cleavage with factor Xa cleavage, enterokinase cleavage, thrombin cleavage, TEV (tobacca etch virus protease) cleavage.

According to the invention, the hydrophobins or derivatives thereof can be used in drilling muds comprising at least one liquid phase. The drilling muds may be any compositions provided that they have at least one liquid phase, especially an oil-based phase. The composition may, in the context of the present invention, also have further phases.

According, to the invention, oil in oil-based drilling muds is preferably biodiesel, an internal olefin, an α-olefin, a vegetable ester, a paraffin or a mixture thereof.

Suitable further solvents are, for example, organic solvents such as ether, aromatic compounds such as toluene, alcohols, alkanes, alkenes, cycloalkanes, cycloalkenes, esters, ketones, naphthenes or halogenated hydrocarbons.

The drilling mud can be adjusted to the type of drilling to be undertaken and, if appropriate, to any substances present in the soil (ores, salts, mineral resources), in order to achieve optimal action. Drilling using the drilling mud can also additionally be promoted by an elevated temperature, for example a temperature of from 0 to 400° C., for example from 30 to 200° C., especially from 40 to 150° C.

The amount of the hydrophobin or derivative thereof used can vary within wide ranges, and the amount is advantageously adjusted to the composition per se and to any further components present in the composition.

The drilling mud (especially its density) has to be adjusted to the particular conditions, for example properties of the formation to be drilled through, the drilling depth, the pressure and the temperature.

It has been found that, surprisingly, even small amounts of a hydrophobin or derivative thereof lead to an improvement in the stability of the drilling muds and hence also of the drilling operation.

According to the invention, the at least one hydrophobin or derivative thereof can be used in any suitable amount. In general, the at least one hydrophobin or derivative thereof is used in an amount of from 0.1 to 10 000 ppm, based on the overall composition, preferably in an amount of from 1 to 1000 ppm, more preferably from 1 to 600 ppm and most preferably from 4 to 500 ppm. In the context of the present application, the unit ppm denotes mg per kg.

The inventive drilling muds can be combined with further customary components and additives. Mention should be made here, for example, of carrier oils without or with marked detergent action.

Suitable mineral carrier oils are the fractions obtained in mineral oil processing, such as brightstock or base oils having viscosities, for example, from the SN 500-2000 class; but also aromatic hydrocarbons, paraffinic hydrocarbons and alkoxyalkanols. Likewise suitable in accordance with the invention is a fraction which is obtained in the refining of mineral oil and is known as "hydrocrack oil" (vacuum distillate cut having a boiling range from about 360 to 500° C., obtainable from natural mineral oil which has been catalytically hydrogenated and isomerized under high pressure and also deparaffinized). Likewise suitable are mixtures of abovementioned mineral carrier oils.

Examples of synthetic carrier oils usable in accordance with the invention are selected from: polyolefins (polyalphaolefins or polyinternal olefins), (poly)esters, (poly)alkoxylates, polyethers, aliphatic polyetheramines, alkylphenol-started polyethers, alkylphenol-started polyetheramines and carboxylic esters of long-chain alkanols. Examples of suitable polyolefins are olefin polymers where Mn=from 400 to 1800, in particular based on polybutene or polyisobutene (hydrogenated or unhydrogenated).

Further suitable carrier oil systems are, for example, described in DE-A 38 26 608, DE-A 41 42 241, DE-A 43 09 074, EP-A 0 452 328 and EP-A 0 548 617, which are hereby incorporated explicitly by reference. The carrier oils mentioned are used in amounts which appear to be suitable to those skilled in the art for the particular application.

Further customary additives are corrosion inhibitors, for example based on ammonium salts of organic carboxylic acids, said salts tending to form films, or on heterocyclic aromatics in the case of nonferrous metal corrosion protection; antioxidants or stabilizers, for example based on amines, further conventional emulsifiers; antistats; metallocenes such as ferrocene; lubricity improvers such as particular fatty acids, alkenylsuccinic esters, bis(hydroxyalkyl) fatty amines, hydroxyacetamides or castor oil; dyes (markers), fluid loss additives (e.g. polymers), substances for adjusting the density, rheology modifiers, and also substances which build up a filtercake (for example bentonite or clay), lime or further emulsifiers. If appropriate amines are also added to lower the pH.

The invention will be illustrated in detail hereinafter by examples.

EXAMPLES

Example 1

Preparations for the Cloning of yaad-$His_6$/yaaE-$His_6$

A polymerase chain reaction was carried out with the aid of the oligonucleotides Hal570 and Hal571 (Hal 572/Hal 573). The template DNA used was genomic DNA of the bacterium *Bacillus subtilis*. The resulting PCR fragment comprised the coding sequence of the *Bacillus subtilis* yaaD/yaaE gene, and an NcoI and BglII restriction cleavage site respectively at each end. The PCR fragment was purified and cut with the restriction endonucleases NcoI and BglII. This DNA fragment was used as an insert and cloned into the vector pQE60 from Qiagen, which had been linearized beforehand with the restriction endonucleases NcoI and BglII. The vectors pQE60YAAD#2/pQE60YaaE#5 thus formed may be used to express proteins consisting of YAAD::$HIS_6$ or YAAE::$HIS_6$.

```
                                           (SEQ ID NO: 25)
Hal570:    gcgcgcccatggctcaaacaggtactga (SEQ ID NO: 26)
Hal571:    gcagatctccagccgcgttcttgcatac (SEQ ID NO: 27)
Hal572:    ggccatgggattaacaataggtgtactagg (SEQ ID NO: 28)
Hal573:    gcagatcttacaagtgccttttgcttatattcc
```

Example 2

Cloning of yaad Hydrophobin DewA-$His_6$

A polymerase chain reaction was carried out with the aid of the oligonucleotides KaM 416 and KaM 417. The template DNA used was genomic DNA of the mold *Aspergillus nidulans*. The resulting PCR fragment comprised the coding sequence of the hydrophobin gene dewA and an N-terminal factor Xa proteinase cleavage site. The PCR fragment was purified and cut with the restriction endonuclease BamHI. This DNA fragment was used as an insert and cloned into the vector pQE60YAAD#2 which had been linearized beforehand with the restriction endonuclease BglII.

The vector #508 thus formed can be used to express a fusion protein consisting of YAAD::Xa::dewA::$HIS_6$.

```
                                           (SEQ ID NO: 29)
KaM416:
GCAGCCCATCAGGGATCCCTCAGCCTTGGTACCAGCGC (SEQ ID NO: 30)
KaM417:
CCCGTAGCTAGTGGATCCATTGAAGGCCGCATGAAGTTCTCCGTCTCCGC
```

Example 3

Cloning of yaad Hydrophobin RodA-$His_6$

The plasmid #513 was cloned analogously to plasmid #508 using the oligonucleotides KaM 434 and KaM 435.

```
                                           (SEQ ID NO: 31)
KaM434:
GCTAAGCGGATCCATTGAAGGCCGCATGAAGTTCTCCATTGCTGC (SEQ ID NO: 32)
KaM435:
CCAATGGGGATCCGAGGATGGAGCCAAGGG
```

Example 4

Cloning of yaad Hydrophobin BASF1-$His_6$

The plasmid #507 was cloned analogously to plasmid #508 using the oligonucleotides KaM 417 and KaM 418.

The template DNA used was a synthetic DNA sequence (hydrophobin BASF1) (see appendix, SEQ ID NO. 11 and 12).

```
                                           (SEQ ID NO: 30)
KaM417:
CCCGTAGCTAGTGGATCCATTGAAGGCCGCATGAAGTTCTCCGTCTCCGC (SEQ ID NO: 33)
KaM418:
CTGCCATTCAGGGGATCCCATATGGAGGAGGGAGACAG
```

Example 5

Cloning of yaad Hydrophobin BASF2-$His_6$

The plasmid #506 was cloned analogously to plasmid #508 using the oligonucleotides KaM 417 and KaM 418.

The template DNA used was a synthetic DNA sequence (hydrophobin BASF2) (see appendix, SEQ ID NO. 13 and 14).

```
                                           (SEQ ID NO: 30)
KaM417:
CCCGTAGCTAGTGGATCCATTGAAGGCCGCATGAAGTTCTCCGTCTCCGC (SEQ ID NO: 33)
KaM418:
CTGCCATTCAGGGGATCCCATATGGAGGAGGGAGACAG
```

Example 6

Cloning of yaad Hydrophobin SC3-His$_6$

The plasmid #526 was cloned analogously to plasmid #508 using the oligonucleotides KaM464 and KaM465.

The template DNA used was cDNA from *Schyzophyllum commune* (see appendix, SEQ ID NO. 9 and 10).

```
                                       (SEQ ID NO: 34)
KaM464:   CGTTAAGGATCCGAGGATGTTGATGGGGGTGC (SEQ ID NO: 35)
KaM465:   GCTAACAGATCTATGTTCGCCCGTCTCCCCGTCGT
```

Example 7

Fermentation of the Recombinant *E. Coli* Strain yaad Hydrophobin DewA-His$_6$ Inoculation of 3 ml of LB liquid medium with a yaad hydrophobin DewA-His$_6$-expressing *E. coli* strain in 15 ml Greiner tubes. Inoculation for 8 h at 37° C. on a shaker at 200 rpm. In each case two 1 l Erlenmeyer flasks with baffles and 250 ml of LB medium (+100 µg/ml of ampicillin) are inoculated with 1 ml in each case of the preliminary culture and incubated for 9 h at 37° C. on a shaker at 180 rpm.

Inoculate 13.5 l of LB medium (+100 µg/ml of ampicillin) with 0.5 l of preliminary culture (OD$_{600\,nm}$ 1:10, measured against H$_2$O) in a 20 l fermenter. At an OD$_{60\,nm}$ of ~3.5, addition of 140 ml of 100 mM IPTG. After 3 h, cool fermenter to 10° C. and centrifuge off fermentation broth. Use cell pellet for further purification.

Example 8

Purification of the Recombinant Hydrophobin Fusion Protein 100 g of cell pellet (100-500 mg of hydrophobin) are made up to total volume 200 ml with 50 mM sodium phosphate buffer, pH 7.5, and resuspended. The suspension is treated with an Ultraturrax type T25 (Janke and Kunkel; IKA-Labortechnik) for 10 minutes and subsequently incubated with 500 units of Benzonase (Merck, Darmstadt; order No. 1.01697.0001) at room temperature for 1 hour to degrade the nucleic acids. Before the cell disruption, filtration is effected with a glass cartridge (P1). For cell disruption and for the scission of the remaining genomic DNA, two homogenizer cycles are carried out at 1500 bar (Microfluidizer M-110EH; Microfluidics Corp.). The homogenate is centrifuged (Sorvall RC-5B, GSA rotor, 250 ml centrifuge cup, 60 minutes, 4° C., 12 000 rpm, 23 000 g), the supernatant was placed on ice and the pellet was resuspended in 100 ml of sodium phosphate buffer, pH 7.5. Centrifugation and resuspension are repeated three times, the sodium phosphate buffer comprising 1% SDS at the third repetition. After the resuspension, the mixture is stirred for one hour and a final centrifugation is carried out (Sorvall RC-5B, GSA rotor, 250 ml centrifuge cup, 60 minutes, 4° C., 12 000 rpm, 23 000 g). According to SDS-PAGE analysis, the hydrophobin is present in the supernatant after the final centrifugation (FIG. 1). The experiments show that the hydrophobin is probably present in the form of inclusion bodies in the corresponding *E. coli* cells. 50 ml of the hydrophobin-comprising supernatant are applied to a 50 ml nickel Sepharose High Performance 17-5268-02 column (Amersham) which has been equilibrated with 50 mM Tris-Cl pH; 8.0 buffer. The column is washed with 50 mM Tris-Cl pH 8.0 buffer and the hydrophobin is subsequently eluted with 50 mM Tris-Cl pH 8.0 buffer which comprises 200 mM imidazole. To remove the imidazole, the solution is dialyzed against 50 mM Tris-Cl pH 8.0 buffer.

FIG. 1 shows the purification of the hydrophobin prepared:

| | |
|---|---|
| Lane A: | Application to nickel-Sepharose column (1:10 dilution) |
| Lane B: | Flow-through = washing step eluate |
| Lanes C-E: | OD 280 Maxima of the elution fractions (WP1, WP2, WP3) |

Lane F shows the applied marker.

The hydrophobin of FIG. 1 has a molecular weight of approx. 53 kD. Some of the smaller bands represent degradation products of the hydrophobin.

Example 9

Performance Testing; Characterization of the Hydrophobin by Change in Contact Angle of a Water Droplet on Glass Substrate:
 Glass (window glass, Süddeutsche glass, Mannheim):
 The hydrophobin purified according to example 8 was used.
 Concentration of the hydrophobin in the solution: 100 µg/ml, the solution further comprised 50 mM of sodium acetate buffer and 0.1% polyoxyethylene(20)-sorbitan monolaurate (Tween® 20), pH of the solution: 4
 Immersion of glass plates into this solution overnight (temperature 80° C.)
 The hydrophobin-coated glass plates are then withdrawn from the solution and washed in distilled water,
 Then incubation 10 min/80° C./1% SDS solution in distilled water
 Washing again in distilled water The samples are dried under air and the contact angle (in degrees) of a droplet of 5 µl of water with the coated glass surface is determined at room temperature.

The contact angle was measured on a Dataphysics OCA 15+ contact angle system, Software SCA 20.2.0. (November 2002). The measurement was effected according to the manufacturer's instructions.

Untreated glass gave a contact angle of 30±5°.

The glass plate coated with the hydrophobin according to example 8 (yaad-dewA-his$_6$) gave a contact angle of 75±5°.

==>Increase in the contact angle: 450

Example 10

Production of an Oil-Based Drilling Mud Comprising a Hydrophobin Concentrate (yaad-Xa-dewA-His$_6$)

The hydrophobin concentrate was added in an amount of
 a) 0 ppm
 b) 10 ppm
 c) 100 ppm
 d) 10 000 ppm to a formulation comprising 222 ml of biodiesel and 61 ml of a calcium chloride solution (25%).

An emulsifying unit (Ultra Turrax T50) was used to produce various emulsions in various test series at the speeds of 2000, 6000 and 10000 rpm and the stirring times of 5 and 10 minutes.

The drilling mud samples were each used to perform emulsion tests (analogously to DIN 51415).

In these tests, the components are mixed with one another, the conditions (stirring time and rotational speed) being specified. Thereafter, the demixing procedure is observed as a function of time.

The evaluation is done with reference to standards, where 1 represents complete splitting of the emulsion, 2 represents partial splitting with release of water, 3 represents undetectable splitting of the emulsion.

In Table 1, results of the tests for the hydrophobin concentrations mentioned are compiled. What are listed in each case are the assessments of the phase separation layers after 1 minute, 24 hours and 48 hours (in each case at room temperature, 23° C.). In addition, tests are also performed at a uniform temperature of 80° C.

TABLE 1

| Example | Conditions | 1 Min | 24 h | 48 h | 24 h, 80° C |
|---|---|---|---|---|---|
| 10 a (comparison) | 5 min. 6000 rpm | 3 | 1 | 1 | 1 |
| 10 a (comparison) | 10 min. 6000 rpm | 3 | 1 | 1 | 1 |
| 10 b | 5 min. 6000 rpm | 3 | 3 | 3 | 1 |
| 10 b | 10 min. 6000 rpm | 3 | 3 | 3 | 1 |
| 10 c | 5 min. 6000 rpm | 3 | 3 | 3 | 2 |
| 10 c | 10 min. 6000 rpm | 3 | 3 | 3 | 2 |
| 10 d | 5 min. 6000 rpm | 3 | 3 | 3 | 2 |
| 10 d | 10 min. 6000 rpm | 3 | 3 | 3 | 3 |

Comment:

Without addition of hydrophobin A, accelerated splitting of the drilling mixture is observed. The evaluation 1 is unacceptable for oil drilling in practice. Even in extremely small amounts, the hydrophobins have a good emulsifying effect. Even 10 ppm of hydrophobin (less than 1 mg) lead to an acceptable result. In the case of use of hydrophobin in higher dosage, even better results are achieved, especially with regard to the thermal stability.

The invention claimed is:

1. A method of improving performance of a drilling mud comprising the step of adding a hydrophobin to a drilling mud.

2. The method of claim 1, wherein the hydrophobin is used functions as an emulsifier in a drilling mud.

3. The method of claim 1, wherein the hydrophobin is a fusion hydrophobin.

4. The method of claim 1, wherein the hydrophobin is a fusion hydrophobin selected from the group consisting of yaad-Xa-dewA-his (SEQ ID NO: 20), yaad-Xa-rodA-his (SEQ ID NO: 22) or yaad-Xa-basf1-his (SEQ ID NO: 24), wherein yaad is optionally a truncated fusion partner yaad' having from 20 to 293 amino acids.

5. The method of claim 1, wherein the hydrophobin comprises from 0.1 to 10,000 ppm of the drilling mud.

6. The method of claim 1, wherein the hydrophobin comprises from 1 to 1000 ppm of the drilling mud.

7. The method of claim 1, wherein the hydrophobin is added to an oil-based drilling mud comprising from 40 to 95% by weight of an oil component and from 2 to 60% by weight of water.

8. The method of claim 1, wherein a component in addition to the hydrophobin is added to improve emulsion formation.

9. A process for drilling a borehole, in which drilling mud comprising a hydrophobin facilitates drilling.

10. The process of claim 9, wherein the hydrophobin is a fusion hydrophobin or a derivative thereof.

11. The process of claim 9, wherein the hydrophobin is a fusion hydrophobin selected from the group consisting of yaad-Xa-dewA-his (SEQ ID NO: 20), yaad-Xa-rodA-his (SEQ ID NO: 22) or yaad-Xa-basf1-his (SEQ ID NO: 24), wherein yaad is optionally a truncated fusion partner yaad' having consisting of from 20 to 293 amino acids.

12. The process of claim 9, wherein the hydrophobin comprises from 0.1 to 10,000 ppm of the drilling mud.

13. The process of claim 9, wherein the hydrophobin comprises from 1 to 1000 ppm of the drilling mud.

14. The process of claim 9, wherein the drilling mud is an oil-based drilling mud comprising from 40 to 95% by weight of an oil component and from 2 to 60% by weight of water.

15. The process of claim 9, wherein the drilling mud is an oil-based drilling mud comprising from 70 to 95% by weight of an oil component and from 2 to 30% by weight of water.

16. The process of claim 9, wherein a component in addition to the hydrophobin is added to improve emulsion formation.

17. A drilling mud comprising a hydrophobin.

18. The drilling mud of claim 17, wherein the hydrophobin is a fusion hydrophobin or a derivative thereof.

19. The drilling mud of claim 17, wherein the hydrophobin used in the drilling mud is a fusion hydrophobin selected from the group consisting of yaad-Xa-dewA-his (SEQ ID NO: 20), yaad-Xa-rodA-his (SEQ ID NO: 22) or yaad-Xa-basf1-his (SEQ ID NO: 24), where yaad is optionally a truncated fusion partner yaad' having consisting of from 20 to 293 amino acids.

20. The drilling mud of claim 17, wherein the hydrophobin comprises from 0.1 to 10,000 ppm of the drilling mud.

21. The drilling mud of claim 17, wherein the hydrophobin comprises from 1 to 1000 ppm of the drilling mud.

22. The drilling mud of claim 17, which is an oil-based drilling mud comprising from 40 to 95 percent by weight of an oil component and from 2 to 60 percent by weight of water.

23. The drilling mud of claim 17, which is an oil-based drilling mud comprising from 70 to 95 percent by weight of an oil component and from 2 to 30 percent by weight of water.

24. The drilling mud of claim 17, wherein a component in addition to the hydrophobin is added to improve emulsion formation.

* * * * *